US011305131B2

United States Patent
Oldham et al.

(10) Patent No.: US 11,305,131 B2
(45) Date of Patent: Apr. 19, 2022

(54) X-RAY PSORALEN ACTIVATED CANCER THERAPY (X-PACT)

(71) Applicants: IMMUNOLIGHT, LLC, Detroit, MI (US); DUKE UNIVERSITY, Durham, NC (US)

(72) Inventors: Mark Oldham, Durham, NC (US); Zakaryae Fathi, Raleigh, NC (US); Wayne F. Beyer, Bahama, NC (US); Frederic A. Bourke, Jr., Aspen, CO (US); Harold Walder, Oak Island, NC (US); Mark DeWhirst, Durham, NC (US); Neil L. Spector, Durham, NC (US); Paul Yoon, Durham, NC (US); Justus Adamson, Durham, NC (US); David Alcorta, Durham, NC (US); Kim Lyerly, Durham, NC (US); Leihua Liu, Durham, NC (US); Takuya Osada, Durham, NC (US)

(73) Assignees: IMMUNOLIGHT, LLC, Detroit, MI (US); DUKE UNIVERSITY, Durham, NC (US)

( * ) Notice: Subject to any disclaimer, the term of this patent is extended or adjusted under 35 U.S.C. 154(b) by 186 days.

(21) Appl. No.: 16/554,831

(22) Filed: Aug. 29, 2019

(65) Prior Publication Data
US 2020/0009398 A1 Jan. 9, 2020

Related U.S. Application Data

(60) Division of application No. 15/434,871, filed on Feb. 16, 2017, now Pat. No. 10,441,810, which is a (Continued)

(51) Int. Cl.
*A61N 5/06* (2006.01)
*A61K 41/00* (2020.01)
(Continued)

(52) U.S. Cl.
CPC ............ *A61N 5/062* (2013.01); *A61K 31/352* (2013.01); *A61K 41/0066* (2013.01); *A61N 5/10* (2013.01);
(Continued)

(58) Field of Classification Search
CPC ...................... A61N 5/062; A61N 5/10; A61N 2005/0661–0662; A61N 2005/1089;
(Continued)

(56) References Cited

U.S. PATENT DOCUMENTS

| 4,960,408 A | 10/1990 | Klainer et al. |
| 8,197,471 B1 * | 6/2012 | Tersigni ............. A61K 41/0052 606/27 |

(Continued)

FOREIGN PATENT DOCUMENTS

| EP | 3 134 122 | 3/2017 |
| JP | 2011-518781 A | 6/2011 |

(Continued)

OTHER PUBLICATIONS

International Search Report and Written Opinion issued in corresponding International Application No. PCT/US16/57685 dated Jan. 19, 2017.

(Continued)

*Primary Examiner* — Thaddeus B Cox
(74) *Attorney, Agent, or Firm* — Oblon, McClelland, Maier & Neustadt, L.L.P.

(57) ABSTRACT

A system for treating a diseased site in a human or animal body. The system includes a pharmaceutical carrier including one or more phosphors which are capable of emitting light into the diseased site upon interaction, a photoactivatable drug for intercalating into DNA of cells at the diseased site, one or more devices which infuse the diseased sited with the photoactivatable drug and the pharmaceutical car- (Continued)

rier, an x-ray or high energy electron source, and a processor programmed to control a dose of x-rays or electrons to the diseased site for production of light inside the tumor to activate the photoactivatable drug.

37 Claims, 16 Drawing Sheets
(13 of 16 Drawing Sheet(s) Filed in Color)

Related U.S. Application Data continuation of application No. PCT/US2016/057685, filed on Oct. 19, 2016.

(60) Provisional application No. 62/243,465, filed on Oct. 19, 2015.

(51) Int. Cl.
  *A61N 5/10* (2006.01)
  *A61K 31/352* (2006.01)
(52) U.S. Cl.
  CPC ............... *A61N 2005/0661* (2013.01); *A61N 2005/0662* (2013.01); *A61N 2005/1089* (2013.01); *A61N 2005/1098* (2013.01)
(58) Field of Classification Search
  CPC ........ A61N 2005/1098; A61K 41/0057; A61K 41/0066
  See application file for complete search history.

(56) References Cited

U.S. PATENT DOCUMENTS

| | | |
|---|---|---|
| 2004/0062754 A1 | 4/2004 | O'Brien et al. |
| 2009/0104212 A1 | 4/2009 | Bourke |
| 2009/0297558 A1 | 12/2009 | Raviv et al. |
| 2010/0016783 A1 | 1/2010 | Bourke, Jr. et al. |
| 2010/0135890 A1 | 6/2010 | Boudou et al. |
| 2010/0164390 A1 | 7/2010 | Ronda |
| 2011/0006212 A1 | 1/2011 | Shchory et al. |
| 2011/0021970 A1 | 1/2011 | Vo-Dinh et al. |
| 2012/0184495 A1 | 7/2012 | Koyakutty et al. |
| 2012/0245565 A1 | 9/2012 | Shachar et al. |
| 2012/0259268 A1 | 10/2012 | Gerrans et al. |
| 2013/0323206 A1 | 12/2013 | Yun et al. |
| 2014/0161824 A1 | 6/2014 | Shneider |
| 2014/0243934 A1 | 8/2014 | Vo-Dinh et al. |
| 2014/0323946 A1 | 10/2014 | Bourke et al. |
| 2015/0196639 A1 | 7/2015 | Lando et al. |
| 2016/0016008 A1 | 1/2016 | Kelly |
| 2016/0067322 A1 | 3/2016 | Schroeder |

FOREIGN PATENT DOCUMENTS

| | | |
|---|---|---|
| WO | WO 2013/009688 A1 | 1/2013 |
| WO | WO 2015/164485 A1 | 10/2015 |

OTHER PUBLICATIONS

Extended European Search Report dated Mar. 20, 2019 in European Patent Application No. 16858126.2, 21 pages
European Office Action dated Apr. 5, 2019 in European Patent Application No. 16858126.2, p. 1.
Sugie, H., et al., "Carbon nanotubes as electron source in an x-ray tube", Applied Physics Letters, vol. 78, No. 17, Apr. 23, 2001, XP012027845, pp. 2578-2580.
Plazas, M.C., et al., "Optical Fiber Detectors as In-Vivo Dosimetry Method of Quality Assurance in Radiation Therapy," Revista Colombiana de Fisica, vol. 37, No. 1, Jan. 1, 2005, XP055233629, pp. 307-313.
Verga, D., et al., "Bipyridyl ligands as photoactivatable mono- and bis-alkylating agents capable of DNA cross-linking", Organic & Biomolecular Chemistry, Jan. 1, 2007, vol.5, No. 2, XP055393113, pp. 233-235
Office Action dated Nov. 2, 2020 in corresponding Japanese Patent Application No. 2018-5392553 (with English Translation), 14 pages
Office Action dated Jan. 8, 2021 in corresponding Indian Patent Application No. 201817014855 (with English Translation), 6 pages.
Office Action dated Dec. 1, 2021 in corresponding European Patent Application No. 16 858 126.2, 9 pages.
European Office Action dated May 13, 2020 in European Patent Application No. 16858126.2, 7 pages.

* cited by examiner

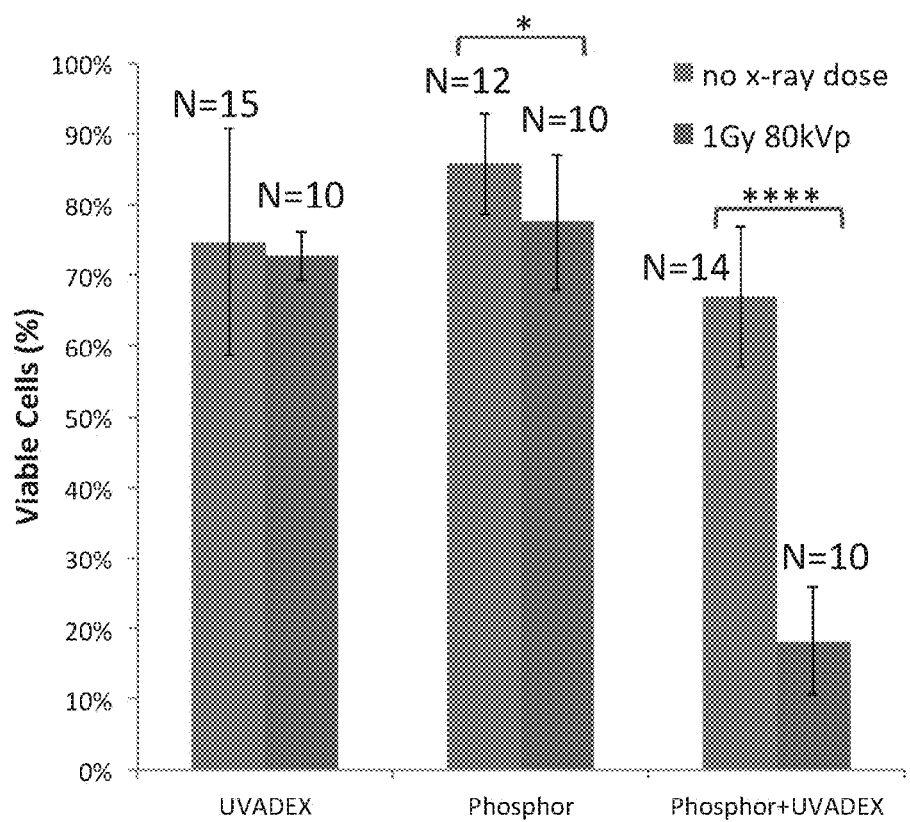

Figure 4A

Fit: Annexin V (+) = A + B [Psoralen] + C [Phosphor] + D [Psoralen] [Phosphor]

| Equation Coefficients | Coefficient Estimate | P-value | |
|---|---|---|---|
| A (intercept) | 3.7E-02 | 0.071 | |
| B (8-MOP effects) | -1.2E-03 | 0.096 | |
| C (phosphor effects) | -5.4E-04 | 0.050 | $R^2$ |
| D (interaction effects) | 5.8E-05 | <.0001 | 0.718 |

X-RAY PSORALEN ACTIVATED CANCER THERAPY (X-PACT)

CROSS REFERENCE TO RELATED APPLICATIONS

This application is a Divisional of U.S. Ser. No. 15/434,871, filed Feb. 16, 2017, now U.S. Pat. No. 10,441,810. This application is related to and claims priority to PCT/US2016/057685, filed Oct. 19, 2016, entitled "X-RAY PSORALEN ACTIVATED CANCER THERAPY (X-PACT)." This application is related to and claims priority to U.S. provisional Ser. No. 62/243,465 filed Oct. 19, 2015, the entire contents of which is incorporated herein by reference. This application is related to U.S. provisional Ser. No. 61/982,585, filed Apr. 22, 2014, entitled "INTERIOR ENERGY-ACTIVATION OF PHOTO-REACTIVE SPECIES INSIDE A MEDIUM OR BODY USING AN X-RAY SOURCE EMITTING LOW ENERGY X-RAYS AS INITIATION ENERGY SOURCE", the entire contents of which are hereby incorporated by reference. This application is related to provisional Ser. No. 62/096,773, filed: Dec. 24, 2014, entitled "INTERIOR ENERGY-ACTIVATION OF PHOTO-REACTIVE SPECIES INSIDE A MEDIUM OR BODY USING AN X-RAY SOURCE EMITTING LOW ENERGY X-RAYS AS INITIATION ENERGY SOURCE," the entire contents of each of which is incorporated herein by reference. This application is related to U.S. provisional Ser. No. 62/132,270, filed Mar. 12, 2015, entitled "TUMOR IMAGING WITH X-RAYS AND OTHER HIGH ENERGY SOURCES USING AS CONTRAST AGENTS PHOTON-EMITTING PHOSPHORS HAVING THERAPEUTIC PROPERTIES", the entire contents of which are hereby incorporated by references. This application is related to U.S. provisional Ser. No. 62/147,390, filed Apr. 14, 2015, entitled "TUMOR IMAGING WITH X-RAYS AND OTHER HIGH ENERGY SOURCES USING AS CONTRAST AGENTS PHOTON-EMITTING PHOSPHORS HAVING THERAPEUTIC PROPERTIES", the entire contents of which are hereby incorporated by references.

This application is related to U.S. Ser. No. 12/401,478 (now U.S. Pat. No. 8,376,013) entitled "PLASMONIC ASSISTED SYSTEMS AND METHODS FOR INTERIOR ENERGY-ACTIVATION FROM AN EXTERIOR SOURCE, filed Mar. 10, 2009, the entire contents of which are incorporated herein by reference. This application is related to U.S. Ser. No. 13/102,277 (now U.S. Pat. No. 9,023,249) entitled "ADHESIVE BONDING COMPOSITION AND METHOD OF USE," filed May 6, 2011, the entire contents of which are incorporated herein by reference. This application is related to provisional Ser. No. 61/035,559, filed Mar. 11, 2008, entitled "SYSTEMS AND METHODS FOR INTERIOR ENERGY-ACTIVATION FROM AN EXTERIOR SOURCE," the entire contents of which are hereby incorporated by reference. This application is related to provisional Ser. No. 61/030,437, filed Feb. 21, 2008, entitled "METHODS AND SYSTEMS FOR TREATING CELL PROLIFERATION DISORDERS USING PLASMONICS ENHANCED PHOTOSPECTRAL THERAPY (PEPST) AND EXCITON-PLASMON ENHANCED PHOTOTHERAPY (EPEP)," the entire contents of which are hereby incorporated by reference. This application is related to non-provisional Ser. No. 12/389,946 (now U.S. Pat. No. 8,951,561), filed Feb. 20, 2009, entitled "METHODS AND SYSTEMS FOR TREATING CELL PROLIFERATION DISORDERS USING PLASMONICS ENHANCED PHOTOSPECTRAL THERAPY (PEPST) AND EXCITON-PLASMON ENHANCED PHOTOTHERAPY (EPEP)," the entire contents of which are hereby incorporated herein by reference. This application is related to non-provisional Ser. No. 11/935,655 (now U.S. Pat. No. 9,358,292), filed Nov. 6, 2007, entitled "METHODS AND SYSTEMS FOR TREATING CELL PROLIFERATION RELATED DISORDERS," and to provisional Ser. No. 60/910,663, filed Apr. 8, 2007, entitled "METHOD OF TREATING CELL PROLIFERATION DISORDERS," the contents of each of which are hereby incorporated by reference in their entireties. This application is related to provisional Ser. No. 61/035,559, filed Mar. 11, 2008, entitled "SYSTEMS AND METHODS FOR INTERIOR ENERGY-ACTIVATION FROM AN EXTERIOR SOURCE," the entire contents of which are hereby incorporated herein by reference. This application is also related to provisional Ser. No. 61/792,125, filed Mar. 15, 2013, entitled "INTERIOR ENERGY-ACTIVATION OF PHOTO-REACTIVE SPECIES INSIDE A MEDIUM OR BODY," the entire contents of which are hereby incorporated herein by reference. This application is further related to provisional Ser. No. 61/505,849 filed Jul. 8, 2011, and U.S. application Ser. No. 14/131,564, filed Jan. 8, 2014, each entitled "PHOSPHORS AND SCINTILLATORS FOR LIGHT STIMULATION WITHIN A MEDIUM," the entire contents of each of which is incorporated herein by reference. This application is related to and U.S. application Ser. No. 14/206,337 (now U.S. Pat. No. 9,488,916), filed Mar. 12, 2014, entitled "INTERIOR ENERGY-ACTIVATION OF PHOTO-REACTIVE SPECIES INSIDE A MEDIUM OR BODY," the entire contents of which are hereby incorporated herein by reference. This application is related to national stage PCT/US2015/027058 filed Apr. 22, 2015, entitled "TUMOR IMAGING WITH X-RAYS AND OTHER HIGH ENERGY SOURCES USING AS CONTRAST AGENTS PHOTON-EMITTING PHOSPHORUS HAVING THERAPEUTIC PROPERTIES," the entire contents of which are hereby incorporated herein by reference.

BACKGROUND OF THE INVENTION

Field of Invention

The invention relates to methods and systems for treating cell proliferation disorders, that provide better distinction between normal, healthy cells and those cells suffering a cell proliferation.

Discussion of the Background

Psoralens are naturally occurring compounds found in plants (furocoumarin family) with anti-cancer and immunogenic properties. Psoralens freely penetrate the phospholipid cellular bilayer membranes and intercalate into DNA between nucleic acid pyrimidines, where the psoralens are biologically inert (unless photo-activated) and ultimately excreted within 24 hours. However psoralens are photo-reactive, acquiring potent cytotoxicity after 'activation' by ultra-violet (UVA) light. When photo-activated, psoralens form mono-adducts and di-adducts with DNA leading to marked tumor cytotoxicity and apoptosis. Cell signaling events in response to DNA damage include up-regulation of $p21^{waf/Cip}$ and p53 activation, with mitochondrial induced cytochrome c release and consequent cell death. Photo-activated psoralen can also induce apoptosis by blocking oncogenic receptor tyrosine kinase signaling, and can affect immunogenicity and photochemical modification of a range of cellular proteins in treated cells.

Importantly, psoralen can promote a strong long-term clinical response, as observed in the treatment of cutaneous T Cell Lymphoma utilizing extracorporeal photopheresis (ECP). In ECP malignant CTCL cells (removed from a patient) are irradiated with ultraviolet A (UVA) light in the presence of psoralen, and then re-administered to the patient. Remarkably, complete long term responses over many decades have been observed in a sub-set of patients, even though only a small fraction of malignant cells were treated. In addition to ECP, psoralens have also found wide clinical application through PUVA treatment of proliferative skin disorders and cancer including psoriasis, vitiligo, mycosis fungoides, and melanoma. Together these results are consistent with an immunogenic role of psoralen in a number of cancers and profilerative disorders.

The cytotoxic and immunogenic effects of psoralen are often attributed to psoralen mediated photoadduct DNA damage. A principle mechanism underlying the long-term immunogenic clinical response likely derives from psoralen induced tumor cell cytotoxicity and uptake of the apoptotic cells by immature dendritic cells, in the presence of inflammatory cytokines. However photochemical modification of proteins and other cellular components can also impact the antigenicity and potential immunogenicity of treated cells.

SUMMARY OF THE INVENTION

In one embodiment, there is provided a system (and associated method) for treating a diseased site in a human or animal body. The system includes a pharmaceutical carrier including one or more energy converters or phosphors which are capable of emitting light into the diseased site or the body upon interaction, a photoactivatable drug for intercalating into DNA of cells at the diseased site, one or more devices which infuse the diseased site with the photoactivatable drug and the pharmaceutical carrier, an x-ray or high energy electron source, and a processor programmed to control a dose of x-rays or electrons to the diseased site for production of light inside the diseased site to activate the photoactivatable drug, wherein the infusion of the photoactivatable drug and the energy converters or phosphors into the diseased site and the dose of x-rays or electrons produces a cytotoxicity inside the diseased site of greater than 20%.

In one embodiment, there is provided a method for treating a tumor (or a diseased site) n a human or animal body. The method includes injecting into a vicinity of and inside the tumor (or a diseased site) a pharmaceutical carrier including one or more phosphors which are capable of emitting light into the tumor or the body upon interaction, infusing the tumor with a photoactivatable drug for intercalating into DNA of cells at the diseased site, applying x-ray or high energy electrons to the tumor (or a diseased site), and producing the light inside the tumor (or a diseased site) to activate the photoactivatable drug and produce, wherein the injection of the photoactivatable drug and the phosphors into the diseased site and the dose of x-rays or electrons beam produces a cytotoxicity inside the diseased site of greater than 20%.

It is to be understood that both the foregoing general description of the invention and the following detailed description arc exemplary, but arc not restrictive of the invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

A more complete appreciation of the invention and many of the attendant advantages thereof will be readily obtained as the same becomes better understood by reference to the following detailed description when considered in connection with the accompanying drawings, wherein:

FIG. 2A is a schematic of cell viability after an X-PACT (X-ray Psoralen Activated Cancer Therapy) treatment as determined by Guava flow cytometry;

FIG. 4A is a schematic depicting a multi-variable linear regression analysis of the resultant Annexin V (+) signal as a function of psoralen concentration and phosphor concentration;

DETAILED DESCRIPTION OF THE INVENTION

Figure 1A:
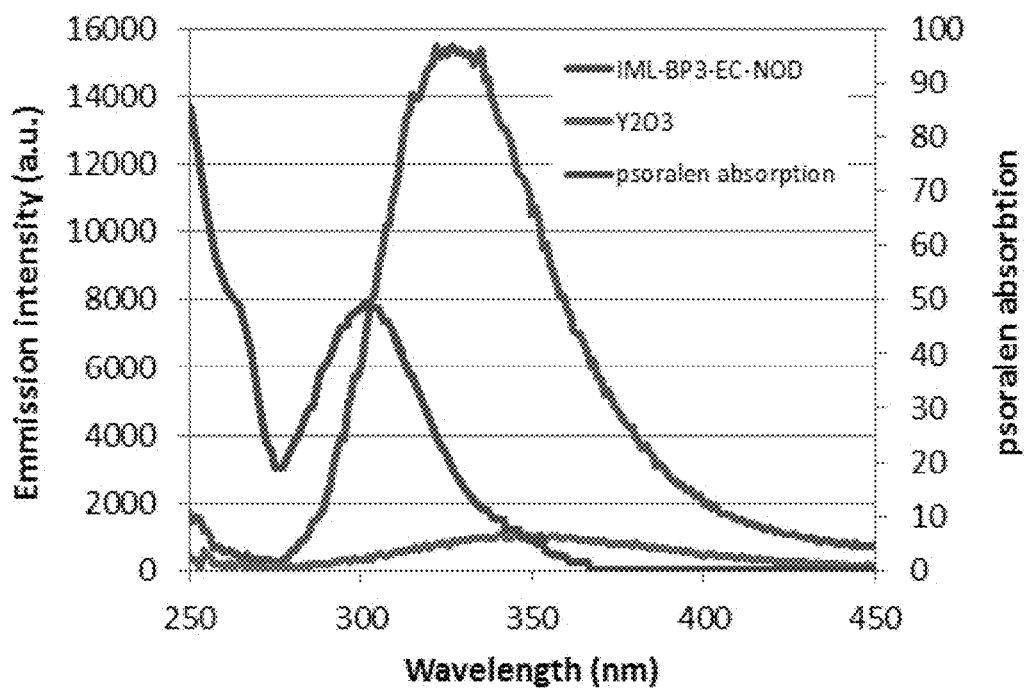
FIG. 1A is a schematic showing the emission of tethered and untethered phosphors under X-ray excitation.

Despite the positive clinical results noted above in extracorporeal applications, use of psoralen traditionally has been restricted to superficial or extra-corporeal applications because of the inability of UVA light to penetrate into tissue (maximum penetration depth <1 mm). In one embodiment of this invention. X-PACT (X-ray Psoralen Activated Cancer Therapy) is utilized to extend psoralen therapy to a wide range of solid tumors, at various depths in tissue. In X-PACT, psoralen is combined with phosphors that absorb and down-convert x-ray energy to re-radiate as UV light or other light such as visible light which can activate a photo-activatable drug at a diseased site. In one embodiment of this invention, relatively low x-ray doses (~1 Gy) are sufficient to achieve photo-activation, greatly reducing the risks of normal tissue damage from radiation.

Accordingly, the present invention sets forth a novel method of treating cell proliferation disorders that is effective, specific, and has few side-effects. Those cells suffering from a cell proliferation disorder are referred to herein as the target cells. In one embodiment of the invention, treatment for cell proliferation disorders, including solid tumors, chemically binds cellular nucleic acids, including but not limited to, the DNA or mitochondrial DNA or RNA of the target cells. For example, a photoactivatable agent, such as a psoralen or a psoralen derivative, is exposed in situ to an energy source (e.g., x-rays) capable of activating energy modulation agents which emit light to activate photoactivatable agents such as psoralen or coumarin.

In one embodiment of the invention, X-PACT activates psoralen with UV light from non-tethered phosphors (co-incubated at the target cell with psoralen). The co-incubation process in one embodiment of the invention involves promoting the presence of psoralen (or other photoactivatable drugs) and the phosphor (energy converters) at a diseased site at the time of the x-ray exposure (or electron beam exposure). Of these two components (the psoralen component and the phosphor component), the psoralen component is more readily passed from the diseased site while the phosphor tends to be retained at the diseased site longer. Accordingly, in one embodiment of the invention, after a coinjection of a phosphor and psoralen mixture, the x-ray exposure would follow within 0.5 to 20 minutes, or 1 to 10 minutes, or 3 to 5 minutes or in general within 20 minutes. Longer times maybe used but at the potential loss in concentration of one of these components from the diseased site. In another embodiment of the invention, a separate injection of psoralen may be provided after the coinjection of the phosphor and psoralen mixture. In another embodiment of the invention, a separate injection of psoralen may be provided after an injection of phosphor alone into the diseased site. In these embodiments with separate psoralen injections, the x-ray exposure would follow within 0.5 to 20 minutes, or 1 to 10 minutes, or 3 to 5 minutes or in general within 20 minutes. Longer times maybe used but at the potential loss in concentration of one of these components from the diseased site.

As noted above, the phosphors absorb x-rays and re-radiate (e.g., phosphoresce) at UV wavelengths. Described below is the efficacy of X-PACT in both in-vitro and in-vivo settings. In-vitro studies utilized breast (4T1), glioma (CT2A) and sarcoma (KP15B8) cell lines. Cells were exposed to X-PACT treatments where the concentrations of drug (e.g., an injection of psoralen and phosphor) were varied as well as the radiation parameters (energy, dose, and dose rate). Efficacy was evaluated primarily using flow cell cytometry. A multi-variable regression on 36 independent irradiation experiments revealed neither psoralen nor phosphor alone had a strong effect on cytotoxicity (Annexin V signal). However, when combined (e.g., an injection of psoralen and phosphor) in X-PACT, a significant increase was observed (p<0.0001), with 82% cytotoxicity compared to just 31% in treated but un-irradiated controls. In-vivo work, utilized X-PACT on BALBc mice with syngeneic 4T1 tumors was conducted, including control arms for X-PACT components. The results demonstrate a pronounced tumor growth delay compared to saline controls (42% reduction at 25 days, p=0.0002).

Accordingly, in one embodiment of the invention, the dose of x-rays or electron beam to the target site of the tumor produces a cytotoxicity of greater than 20%, greater than 30%, greater than 50%, greater than 60%, greater than 70%, greater than 80%. In one embodiment of the invention, the dose of x-rays or electrons to the target site of the tumor produces a cytotoxicity between 20% and 100%, between 40% and 95%, between 60% and 90%, or between 70% and 80%. The cytotoxicity can be categorized into components involving 1) the toxicity of the phosphor itself without psoralen and 2) the apoptosis-induced cell death generated by UV activation of the psoralen. The apoptosis-induced cytotoxicity can range from greater than 20%, greater than 30%, greater than 50%, greater than 60%, greater than 70%, greater than 80%. In one embodiment of the invention, the apoptosis-induced cytotoxicity can range between 20% and 100%, between 40% and 95%, between 60% and 90%, or between 70% and 80%.

Medical applications of ionizing radiation have traditionally associated with diagnostic imaging and radiation therapy. Diagnostic imaging (planar x-rays and x-ray-CT) utilizes low energy x-rays, in order to obtain better soft-tissue-bone contrast, and lower dose exposure to the patient. In radiation therapy, higher energy MV radiation (6MV and higher) is typically used to achieve skin sparing. The X-PACT therapeutic paradigm, in one embodiment of this invention, departs from these conventions by utilizing low energy radiation (and low doses) to initiate phosphorescence of UV light in-situ, in potentially deep seated lesions, for the purpose of activating a potent anti-tumor photo-bio-therapeutic (psoralen). In one embodiment of the invention, X-PACT produces measurable anti-tumor response without the need for complicate 1.1 Phosphors and X-Ray Stimulation of UV Light In one embodiment of the present X-PACT therapy, psoralen is activated by light generated in-situ from phosphor particles undergoing x-ray stimulated phosphorescence. The emission profiles from the phosphor preferably overlap the absorption/activation wavelengths of psoralen. While nano-scintillating particles have been developed which were tethered to psoralen, in one embodiment of this invention, a treatment system does not necessarily (but could) use tethered phosphors. In the embodiment without tethering, the functionally of the tethering is replaced by the above-noted co-incubation of psoralen and phosphor particles at the target or diseased site, as described above. The untethered psoralen benefits from a high degree of mobility and greater intercalation with DNA. In one embodiment, phosphors of different particle size and distribution are utilized or specific absorption and emission spectra.

In one embodiment of the invention, the phosphors shown in FIG. 1A, (i.e., $YTaO_4$ coated with ethyl cellulose) may be used. As shown in FIG. 1, the emission spectra of the $YTaO_4$ phosphor overlaps with the wavelength required to activate psoralen (~300-340 nm). FIG. 1 shows that the emission under X-Ray excitation of the $YTaO_4$ phosphor is ~16 times brighter than a tethered nanoparticles $Y_2O_3$ phosphor. In one embodiment of the invention, both of the phosphors (as shown in FIG. 1) have output wavelengths that "match" the absorption spectrum of the bio-therapeutic agent to be activated (in this case the psoralen). In one embodiment of the invention, a variety of bio compatible coatings can added to the phosphors to provide biological inertness while maintaining sufficient transparency in the UV range, thus maintaining the ability of the in vivo generated UV light to activate psoralen. In one embodiment of the invention, the phosphors can be made from an inert lattice structure, which may not require a bio compatible coating.

1.2 Psoralen

Both commercially available UVADEX (formulated 8-MOP psoralen) and pure 8-MOP were used as alternative formulations of psoralen agents. Prior work has shown that the number of DNA photo-adducts is a linear function of the product of 8-MOP (psoralen) concentration and light-exposure. UVADEX and 8-MOP concentrations in the range 10-60 μM were evaluated. The stability of drug in the presence of phosphors was investigated using standard UV-Vis spectroscopy and HPLC-MS.

1.3.1 In-Vitro X-PACT Studies

Guava Annexin V flow cell cytometry was used to quantify cytotoxic in 3 murine tumor cell lines (breast –4T1, glioma-CT2A, and sarcoma KP15B8). In-vitro X-PACT studies were conducted on cells prepared in the following manner. Cells were incubated in appropriate growing media and buffers before being trypsinized and plated evenly onto twelve (12) well plates for 24 hours. About 20 minutes prior to X-PACT irradiation, the wells of each plate were exposed to the following combinations of additives: (1) control-cells only with no additives, (2) UVADEX only, (3) phosphors only, (4) UVADEX+phosphors. Each plate had twelve (12) wells with three wells for each of the four treatment arms. The plates were then irradiated with x-rays by placing the plate at a known distance from the x-ray source (e.g., 50 cm). After irradiation the cells were incubated on the plate for 48 hours prior to performing flow cytometry. For compatibility with 96-well Guava Nexin® assay, the remaining cells were again trypsinized (after the 48 hour incubation) and plated onto a 96-well plate. The phosphors used in this evaluation were designated as NP 200 and GTP 4300. These phosphors have the following elemental compositions, as shown in Table 1 below:

GTP4300=Ca,F,Cl,PO4,(96-99%)

Mn(1-3%)Sb(<1%)

$Zn_2SiO_4$:Mn with Mn doped between 0.05-10%.)

TABLE 1

|  | | % Viability (1-Toxicity) | Psoralen & Phosphor | Fractional Kill |
|---|---|---|---|---|
|  | $Zn_2SiO_4$:Mn | 75% | 0.51 | 32.0% |
| GTP 4300 | $3Ca_3(PO4)_2 \cdot Ca(Fl,Cl)_2$: $Sb^{3+}, Mn^{2+}$ | 70% | 0.54 | 22.9% |

Fractional kill: Added cell kill by the combination of Psoralen and phosphor and X-Ray In one embodiment of the invention, the phosphors are mixed in combination at a ratio of 2 parts by weight of GTP 4300 for every one part by weight of $Zn_2SiO_4$:Mn.

X-ray stimulated emission from this combination of phosphors was taken from the following slurry using the following procedures Acetic acid diluted in di-ionized water at a rate of 1:10 by weight or by volume was prepared. A total of 2 mL of the diluted acetic acid solution was added to 0.3 grams of the combined phosphors. The slurry hence formed was stirred using a vortex mixer for at least 60 sec. The high viscosity slurry exhibits paste-like behavior from a viscosity standpoint. The test tube containing the slurry was then set inside an X-Ray chamber to be exposed to X-Ray energy radiation produced by using a 6 mA beam at a voltage of 125 kV. The test tube was placed at a distance from the X-Ray source of 20 cm. The fiber optic probe of a photo-spectrometer feeding to an ICCD camera was inserted inside the tube and was brought to a close proximity to the pasty slurry at a distance of 2 mm approximately. The fiber probe was then fixed in place using an adhesive tape. The X-Ray energy was turned on and the emission out of the slurry was collected.

Figure 1B:
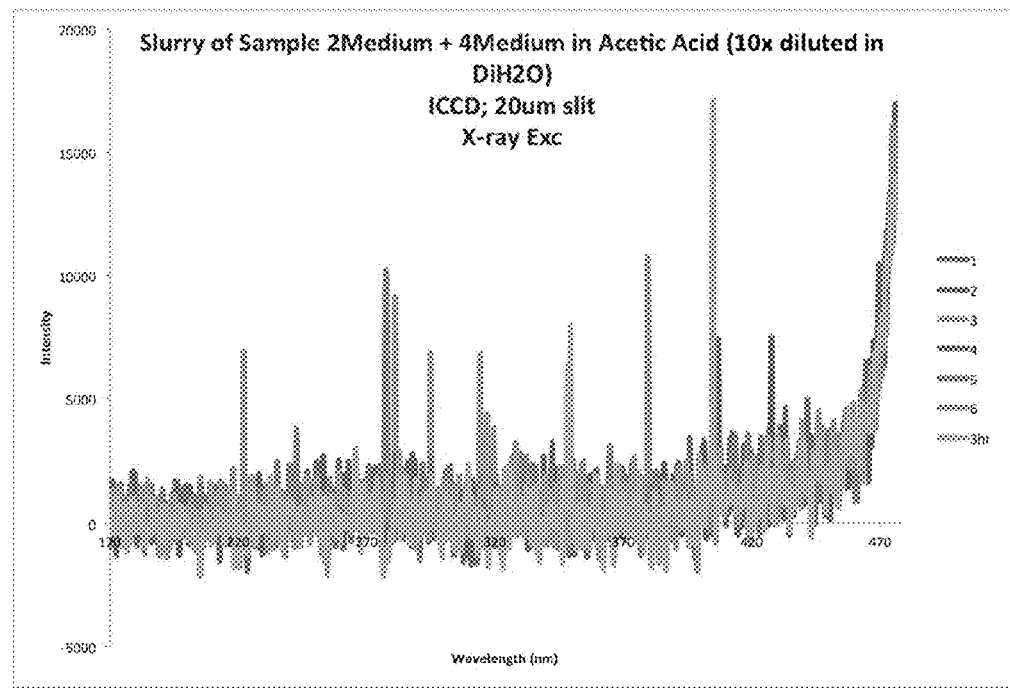
FIG. 1B is a schematic showing UV emission under X-Ray energy of a combined GTP 4300 and for $Zn_2SiO_4$:Mn phosphor.
Figure 1C:
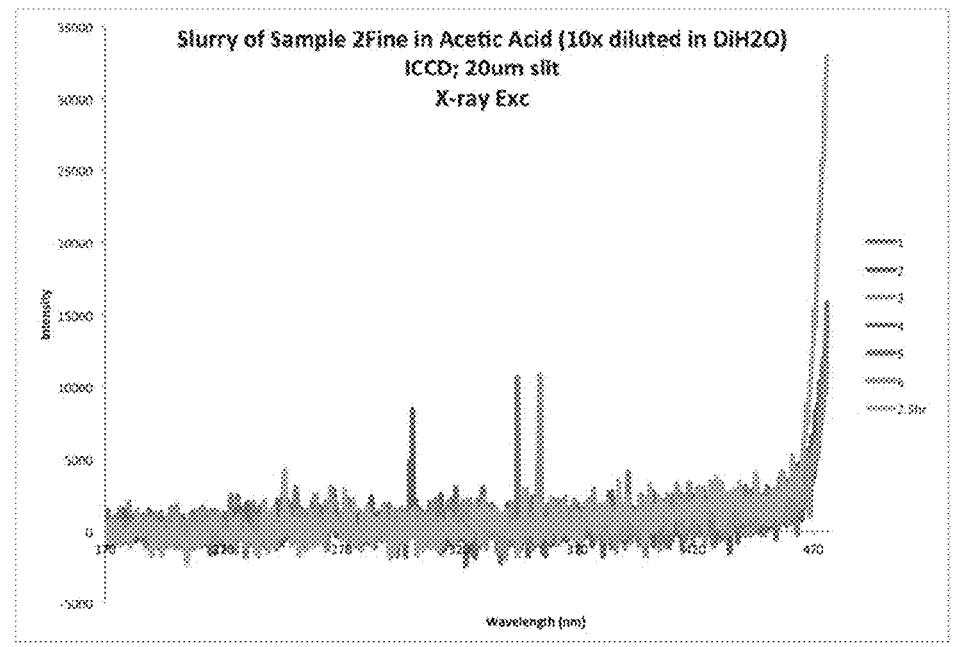
FIG. 1C is a schematic showing UV emission under X-Ray energy $Zn_2SiO_4$:Mn.
Figure 1D:
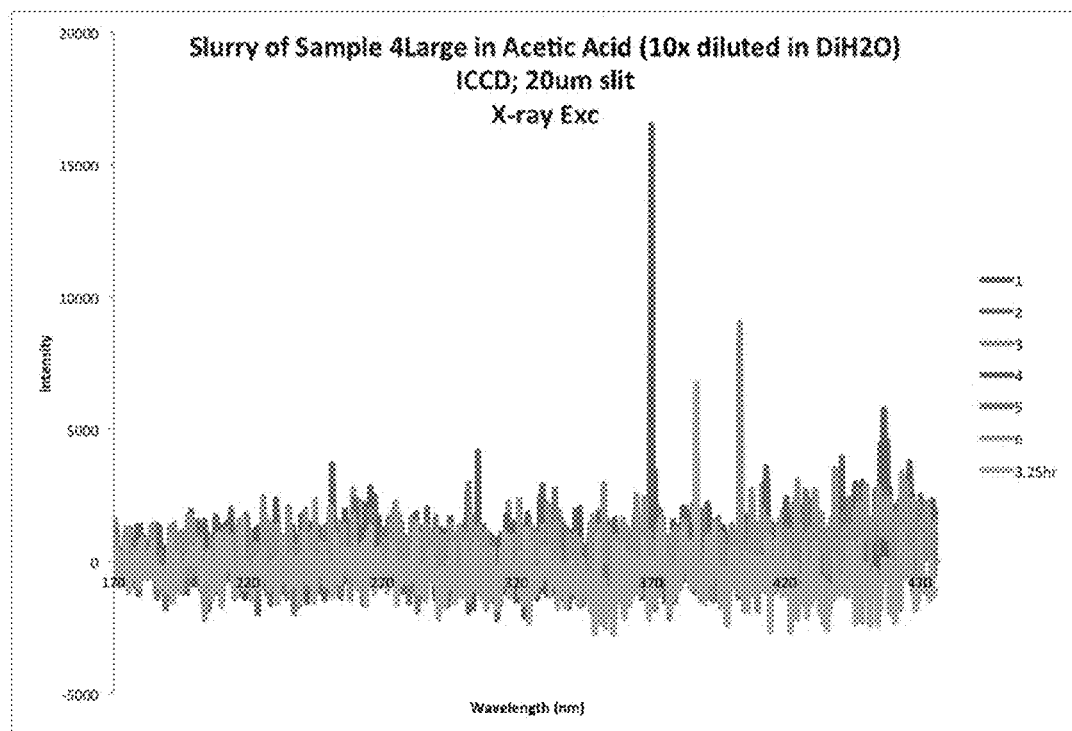
FIG. 1D is a schematic showing UV emission under X-Ray energy for GTP 4300 phosphor.
Figure 1E:
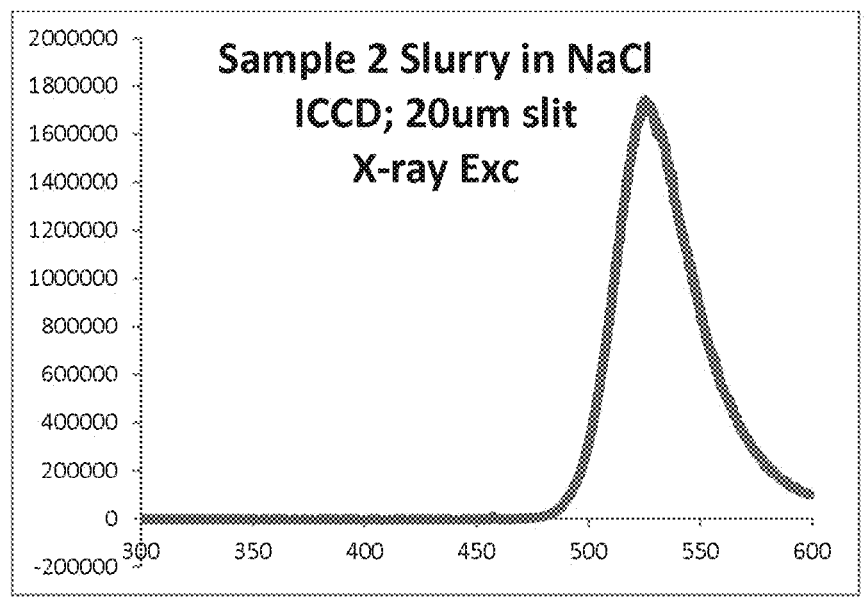
FIG. 1E is a schematic showing UV and visible emissions under X-Ray energy for $Zn_2SiO_4$:Mn in a NaCl slurry.
Figure 1F:
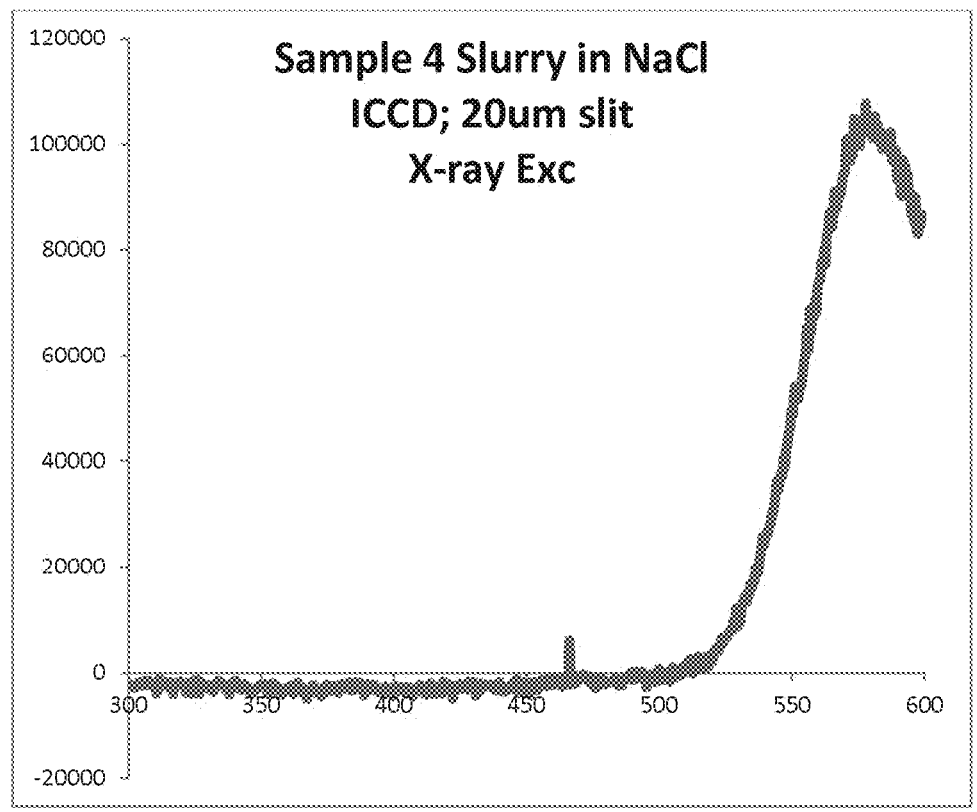
FIG. 1F is a schematic showing UV and visible emissions under X-Ray energy GTP 4300 in a NaCl slurry.
Figure 1G:
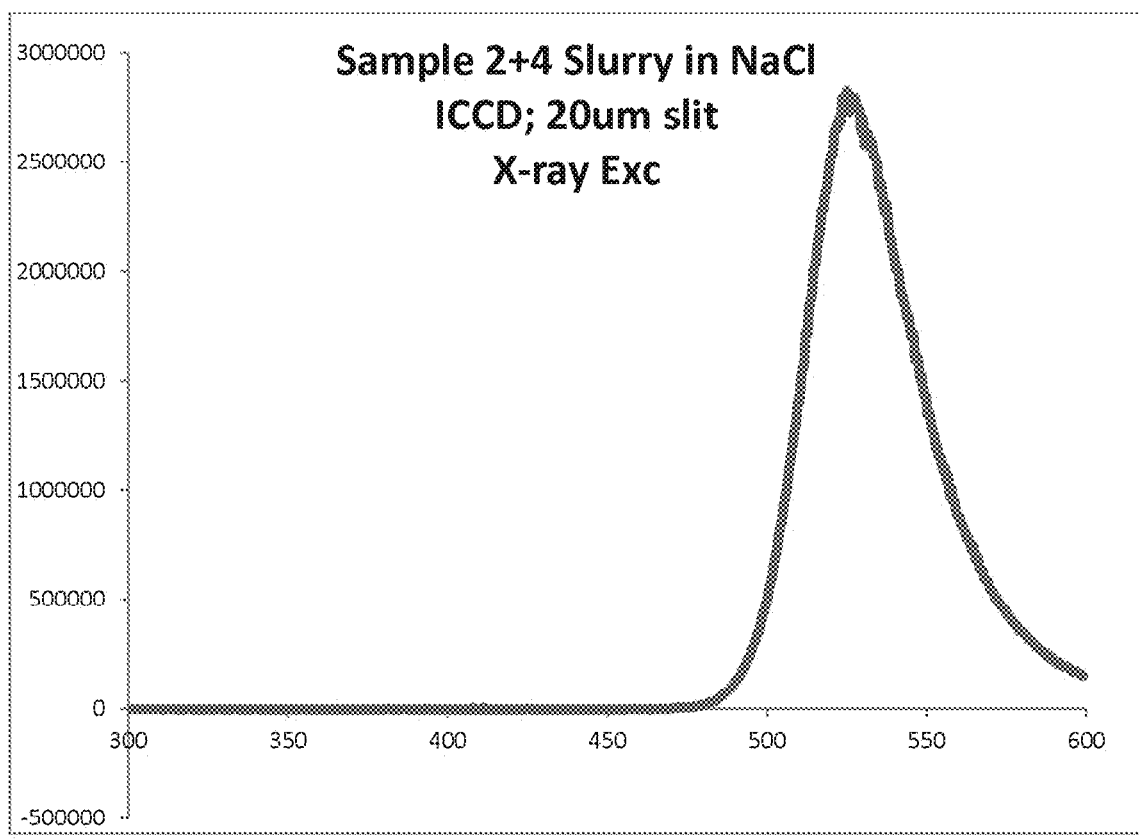
FIG. 1G is a schematic showing UV and visible emissions under X-Ray energy of the combined phosphors in a NaCl slurry.

Several emissions were collected. The slurry was found to emit both in the visible and the UV range as illustrated in FIG. 1B, showing UV emission under X-Ray energy of a combined GTP 4300 and for $Zn_2SiO_4$:Mn phosphor. The emissions measurements were collected 1, 2, 3, 4, 5, 6 hours after the slurry was made. Under similar conditions of preparation the slurry made of the individual phosphors ($Zn_2SiO_4$ and GTP 4300) is presented in FIGS. 1C and 1D (respectively). Visible emissions are stronger than the UV emission of both materials. FIG. 1E is a schematic showing UV and visible emissions under X-Ray energy $Zn_2SiO_4$:Mn in a NaCl slurry. FIG. 1F is a schematic showing UV and visible emissions under X-Ray energy GTP 4300 in a NaCl slurry. FIG. 1G is a schematic showing UV and visible emissions under X-Ray energy of the combined phosphors in a NaCl slurry.

Figure 1H:
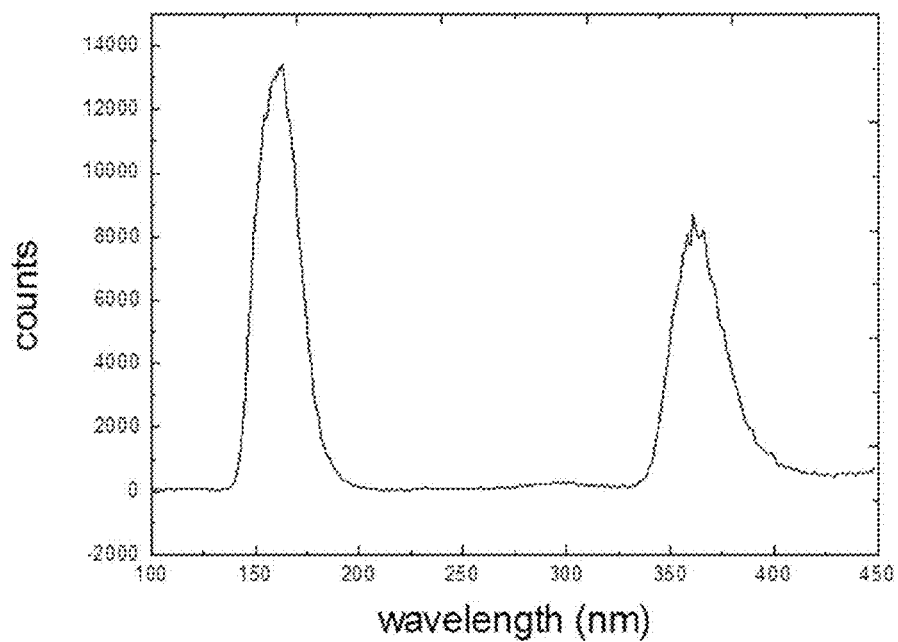
FIG. 1H is a schematic showing cathodoluminescence for the $Zn_2SiO_4$phosphor discussed above.
Figure 1I:
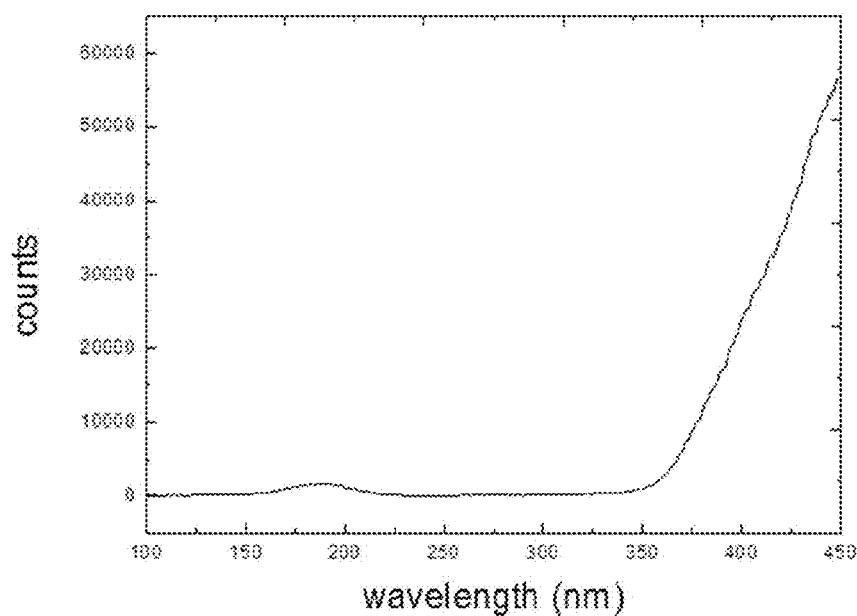
FIG. 1I is a schematic showing cathodoluminescence for the GTP 4300 phosphor discussed above.

FIG. 1H compares cathodoluminescence for the $Zn_2SiO_4$:Mn phosphor discussed above. FIG. 1I compares cathodoluminescence for the GTP 4300 phosphor discussed above.

Regardless of phosphor, the following injections shown in Table 2 were illustrative of the concentration used as a function of the measured or predicted tumor volume (or the calculated volume of the diseased site). In these evaluations, vials of sterilized phosphor were mixed with UVADEX™ (100 μg/mL 8-MOP) as the sole diluent.

TABLE 2

| Tumor volume | mL of slurry per $cm^3$ tumor | | milligrams of phosphor per $cm^3$ of tumor | | Total volume injected |
|---|---|---|---|---|---|
|  | Min | Max | Min | Max |  |
| 8-15 cubic centimeters | 0.034 | 0.063 | 0.333 | 0.625 | 0.5 mL |
| 15-29.9 cubic centimeters | 0.033 | 0.067 | 0.334 | 0.667 | 1 mL |
| 30-49.9 cubic centimeters | 0.040 | 0.067 | 0.401 | 0.67 | 2 mL |
| 50-74.9 cubic centimeters | 0.040 | 0.060 | 0.401 | 0.600 | 3 mL |
| 75-99.9 cubic centimeters | 0.040 | 0.053 | 0.400 | 0.533 | 4 mL |
| >100 cubic centimeters | 0.044 | 0.050 | 0.435 | 0.500 | 5 mL |

1.3.2 In-Vitro Radiation Activation Technique

A range of x-ray activation protocols were investigated to determine X-PACT cytotoxic efficacy in relation to x-ray energy (kVp), total dose, and dose-rate. kVp beam energies ranging between 80 and 100 kV were investigated. kV beams were obtained from various x-ray generating equipment, including orthovoltage units, standard diagnostic radiographic, fluoroscopic, and cone-beam computed tomography (CBCT) systems. The primary kV x-ray source was a Varian on-board-imaging x-ray source commonly found on Varian medical linear accelerators. In one embodiment of the invention, the x-ray dose may be relatively low (~1 Gy/fraction for 9 fractions). This low-dose requirement (as compared to conventional radiation therapy) provides in this embodiment safe delivery of the radiation component of X-PACT. In this embodiment, normal tissue tolerances (skin, bone) can be kept within tolerance doses. In one embodiment of the invention, the x-ray doses can specifically range from 0.2-2 Gy, with preferred doses of 0.5-1 Gy.

For x-ray irradiation, the well plates were positioned at a set distance (e.g., typically 50 cm) from the x-ray source on a solid water phantom and the position of the well plates within the x-ray beam was verified by low dose kV imaging. Irradiations were typically delivered in a "radiograph" mode; where multiple pulses of a set mA (e.g., typically 200 mA) and ms (e.g., typically 800 ms) and pulses were delivered e.g., every 5-15 seconds. In one embodiment, the radiation can be delivered in a "pulsed fluoroscopy mode" (e.g., at 10 Hz) at the maximum mA setting. In one embodiment, kVp settings of 80 and 100 kVp (and ranges in between) with no added filtration in the beam (Half Value Layer=3.3 and 3.9 mm Al, respectively) are suitable for the invention. Higher kVps and lower kVps can be used.

1.3.3 In-Vitro Analysis: Quantification of Cytotoxicity and Apoptosis

Two primary flow cytometry metrics were used to evaluate the X-PACT treatments, both determined at 48 h after X-PACT treatment. Cells plated in 12-well plates, where individual wells in each plate may receive different experimental conditions (e.g. psoralen concentration), but the same x-ray dose (i.e. all wells in a given plate receive the same x-ray dose). The first metric is metabolically viable cell count (or cell viability) determined from the number of whole cells per well as determined using forward scattering (FSC). For each well, the cell viability was normalized to that in a control well on the same plate, which had no additives but did receive the radiation of that plate. (All wells on a given plate receive the same dose.) The second metric is Annexin V (+) signal, which is the fraction of the metabolically viable cells which expressed a positive Annexin V signal as determined by flow cell cytometry, and include any cells advancing toward early or late apoptotic cell death. The Annexin V (+) signal was corrected by subtracting the control signal from the "no-additive" well on the same plate. For both metrics, correcting for the control on the same plate, minimizes any potential inter-plate systematic bias associated with plating constancy or Annexin V gating parameters. The majority of plots in the results either use metabolically viable cell count or Annexin V(+) signal as defined by Krvsko, Vanden Berghe, D'Herde, & Vandenabeele, 2008.

Metabolic cell viability was also assessed visually using Methylene blue staining and ATP-induced Luminescence imaging (Cell-Titer-Gb® Luminescence Cell Viability Assay). The luminescence imaging permitted investigation of the cytotoxicity of psoralen activated directly with a UV lamp, and in the absence of phosphors and x-ray radiation.

Several statistical analyses were evaluated, including unequal variance two-sample t-tests, Analysis of Variance (ANOVA), and multi-variable regression. The unequal variance two-sample t-test tests the null hypothesis that the means of observations (e.g. viable cells, Annexin V signal) in two different populations are equal. The p-value gives the probability that the observed difference occurred by chance. The lower the p-value, the less likely the observed difference occurred by chance. Multi-variable regression was used to test the null hypothesis that psoralen and phosphor had no effect on Annexin V (+) signal and to test if there is a first-order interaction between the two therapeutic elements. Non-parametric statistical analysis were also evaluated for each test, and showed consistent results.

The results of statistical analyses were classified in four categories: weakly significant, moderately significant, significant, and very significant. A single asterisk indicates weakly significant statistics (*), where the p-value is in the range $0.01<p<0.05$. Double asterisks indicate moderately significant statistics (), where $0.001<p<0.01$. Triple asterisks indicate significant statistics (*), where $0.0001<p<0.001$. Quadruple asterisks indicate very significant statistics (****), where $p<0.0001$. This convention will be used throughout the remaining description.

1.3.4 In-Vivo X-PACT Experiments

An in-vivo trial was conducted for preliminary evaluation of X-PACT administered to syngeneic 4T1-HER2 tumors grown on BALB/c mice. There were 4 arms of the trial: (1) saline only (control), (2) phosphors alone with x-ray, (3) psoralen (AMT) alone with x-ray, and (4) full X-PACT treatment including both phosphor and psoralen and x-ray irradiation. X-PACT treatments were given in 3 fractions per week, to a total of 6 fractions. In arms 2-3 a consistent x-ray irradiation technique was used (about 1.2 Gy delivered at 75 kVp by 30 mA in 3 minutes) with 100 μg of phosphor, and 5 μM psoralen (AMT) (with μM representing micromolar). 0.5 Million tumor cells were injected per mouse. There were 6-8 mice per arm, and the study was repeated a second time, yielding effective sample sizes of 12-16.

2.1 X-PACT: In-Vitro Studies

Figure 2B:
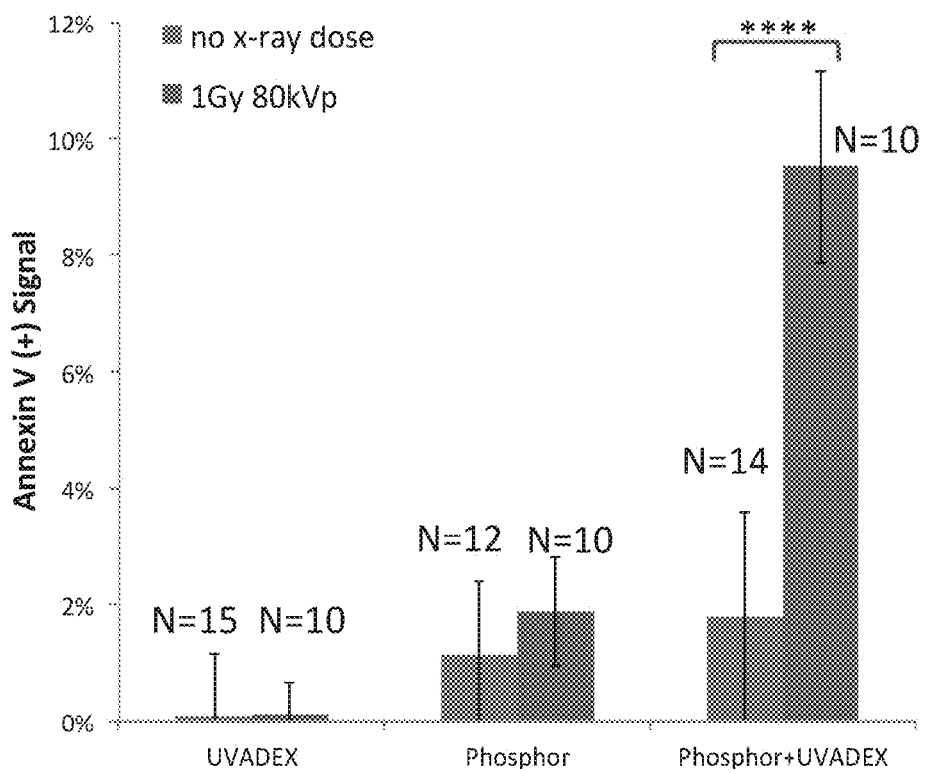
FIG. 2B is a schematic depicting the Annexin V (+) fraction of viable cells shown in FIG. 2A.
Figure 2C:
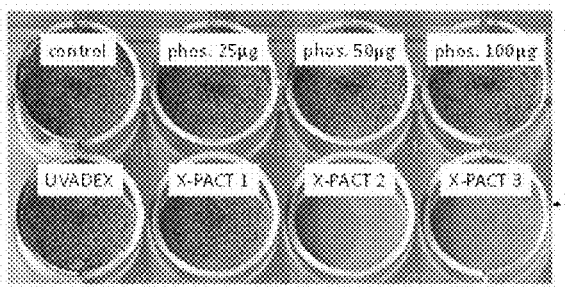
FIGS. 2C and 2D are depictions of cell viability illustrated by methyl blue staining for identical plates each receiving 1 Gy of 80 kVp X-rays.
Figure 2D:
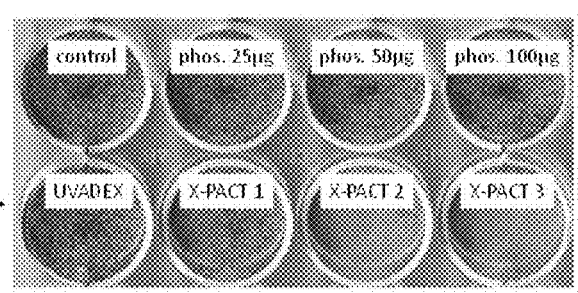

FIGS. 2A-2D illustrate the efficacy of X-PACT treatment ill-vitro in 4T1-HER2 cells, utilizing an X-PACT regimen of 1/10-diluted UVADEX (with equivalent of 10 μM 8-MOP), 50 μg/mL phosphor-0.6 Gy of 80 kVp x-rays. FIG. 2A presents the cell viability data for three treatment conditions: UVADEX alone, phosphors alone, and the X-PACT combination of UVADEX and phosphors (10 μM 8-MOP equivalent dilution of UVADEX, 50 pig/mL phosphor, 0.6 Gy of 80 kVp radiation). The data were compiled from experiments performed on 5 different days (within 1 month), including 15 separate experimental and 10 control plate irradiations. FIG. 2B presents the Annexin V (+) signal for the same three conditions as in FIG. 2A. FIGS. 2C and 2D show corresponding images of viable cell populations revealed by methylene blue staining. Two results from two separate plates are shown, each with identical preparations to investigate reproducibility. X-PACT variants were tested corresponding to three concentrations of phosphor (25, 50, and 100 μg/mL) with the UVADEX concentration fixed at 1/10 dilution (10 uM 8-MOP).

2.1.1 In-Vitro X-PACT and Other Cell Lines

Figure 3A:
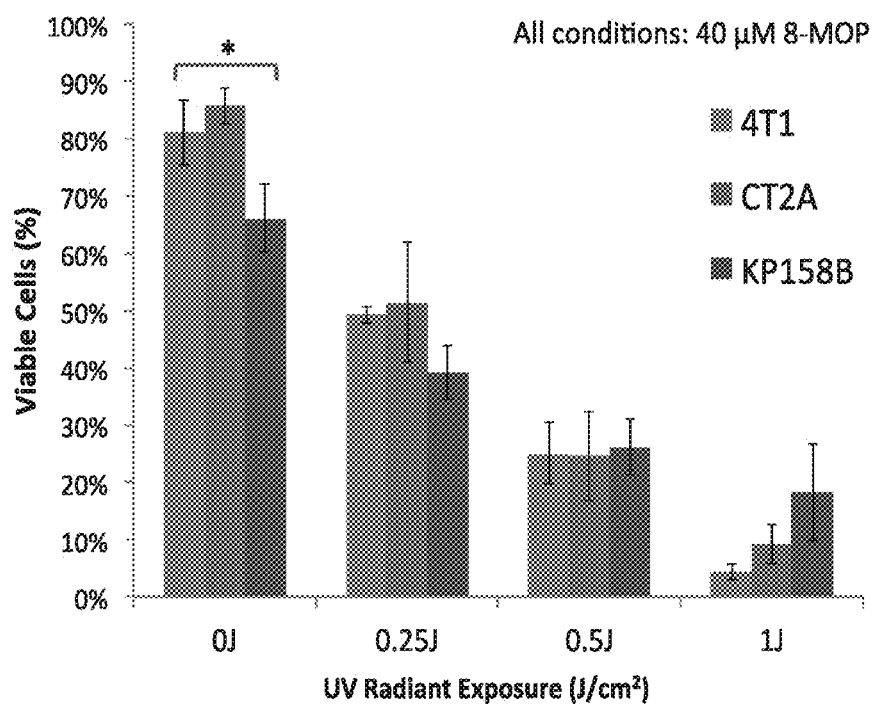
FIG. 3A is a schematic depicting the percentages of cell survival after UV light exposure.
Figure 3B:
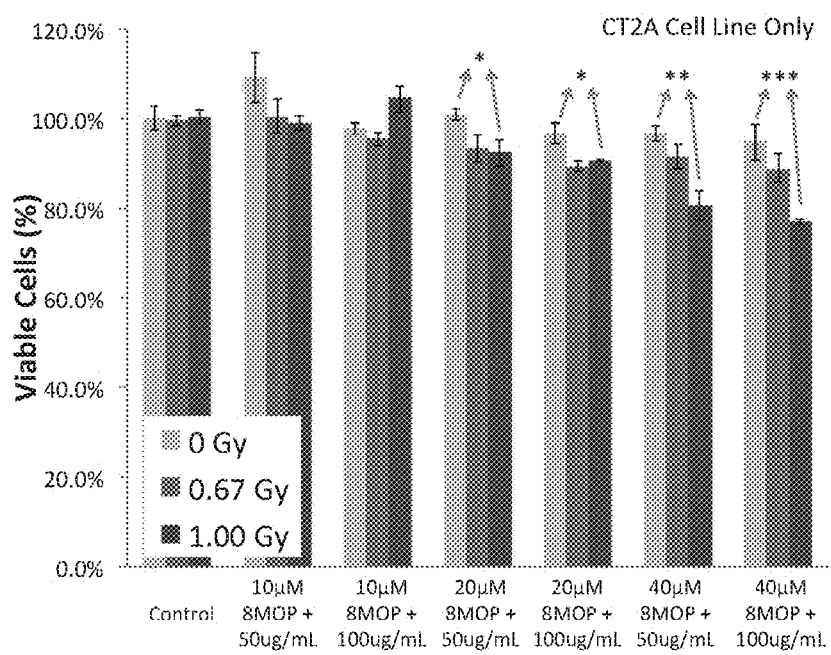
FIG. 3B is a schematic depicting, for CT2A cells, the X-PACT cytotoxicity under different X-ray doses, different concentrations of 8-MOP psoralen, and different concentration of phosphor.

The relative effectiveness of UV activated psoralen on three (3) independent cell lines is shown in FIGS. 3A and 3B. FIG. 3A shows comparable sensitivity of CT2A (murine malignant glioma), 4T1 and KP158B (sarcoma) cell lines to light-activated psoralen, which is one of the therapeutic mechanisms of X-PACT. More specifically, FIG. 3A shows the effect of UV light activated psoralen was to reduce viable cells in 3 cell lines (data from Cell-Titer-Glo® Luminescence Cell Viability Assay under UV light). N=4 for each cell line at each UV light condition (0, 0.25, 0.5, 1.0 $J/cm^2$). The psoralen concentration was 40 μM.

FIG. 3B presents data on CT2A malignant glioma cells, for a range of X-PACT parameters including variable x-ray dose (0, 0.67 and 1 Gy), phosphor concentration (650 or 100 μg) and psoralen concentration (8-MOP) at 10, 20 and 40 μM respectively.

2.1.2 In-Vitro X-PACT: Psoralen and Phosphor Concentration

FIG. 4A presents a multi-variable linear regression analysis on 36 independent measurements (wells) of Annexin V (+) as a function of two variables: psoralen concentration, and phosphor concentration. All samples received an x-ray dose of 1 Gy at 80 kVp. Psoralen and phosphor concentrations ranged from 10 μM to 50 μM and from 25 μg to 200 μg respectively. The fitting equation is given at the top of the Table and in Equation 1. The overall fit was statistically significant as were each of the fit coefficients. All of the 36 X-PACT wells were irradiated with 1 Gy of x-ray radiation at 80 kVp. The fit had the following form given in Equation 1 (where P=phosphor, and Conc=concentration):

$$\text{Annexin } V(+) = A + B^*[\text{8-MOP Conc}] + C^*[P\text{Conc}] + D^*[\text{8-MOP Conc.}]^*[P\text{Conc.}] \quad \text{Eq 1}$$

Figure 4B:
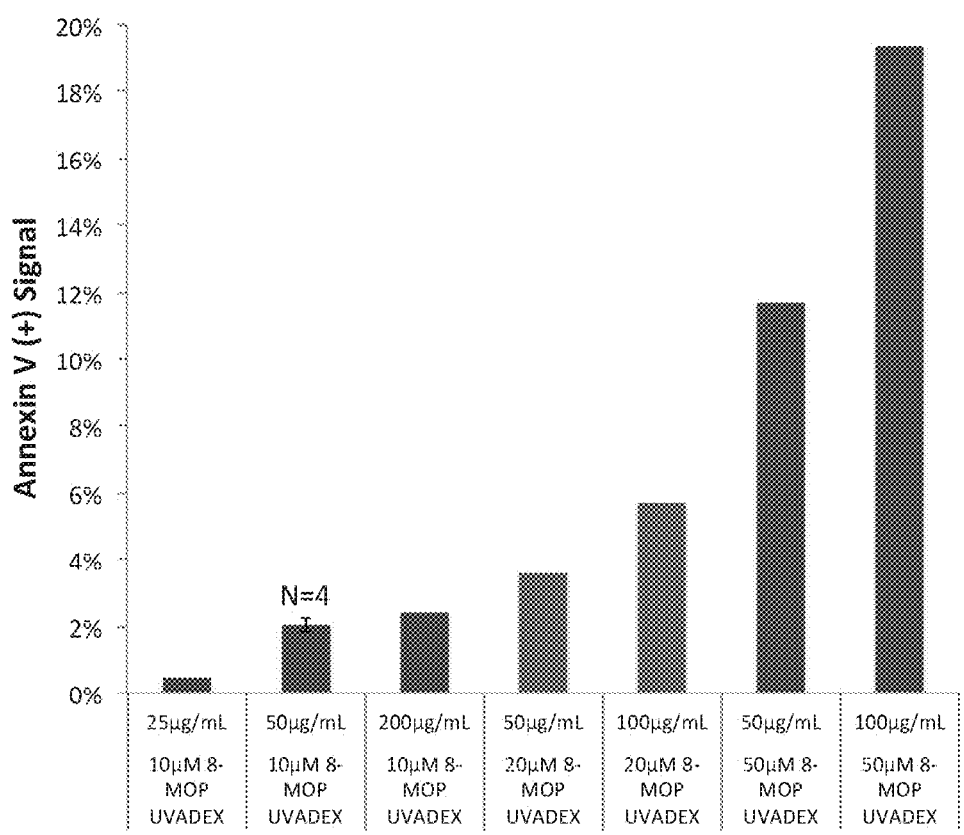
FIG. 4B is a schematic depicting a subset of data demonstrating the magnitudes and effects of increasing concentrations of psoralen and phosphor on the Annexin V (+) signal.

FIG. 4B shows a subset of data, collected on one day, demonstrating the magnitudes and effects of increasing concentrations of psoralen and phosphor on Annexin V (+) signal. More specifically. FIG. 4B is a subset of the data in FIG. 3A that was collected on a single day, indicating magnitude and trends. UVADEX (100 μM 8-MOP) was diluted to 10, 20, and 50 μM, or 1:10, 1:5, and 1:2 UVADEX. Four repeats (N=4) were performed for the condition with 50 μg/mL of phosphor and 10 μM of 8-MOP diluted from UVADEX.

2.1.3 In-vitro X-PACT: X-ray Energy and Total Dose

Figure 5:
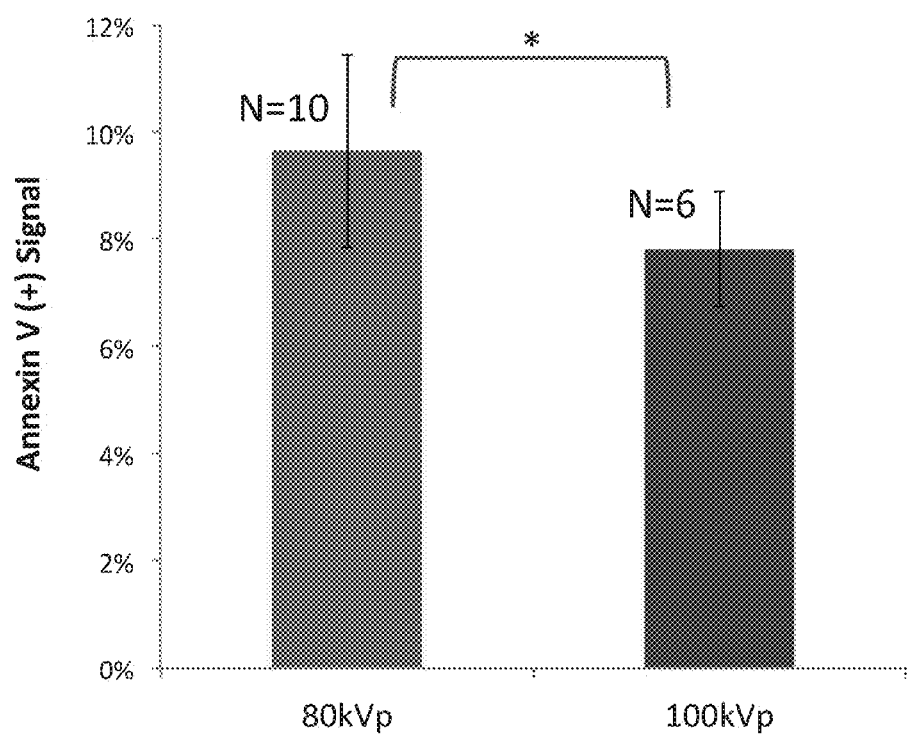
FIG. 5 is a schematic depicting the results of an X-PACT application to 4T1-her2 observed at both 80 and 100 kV.

FIG. 5 compares X-PACT at two different x-ray energies (80 and 100 kVp). An X-PACT effect in 4T1-her2 was observed at both 80 and 100 kV, with the 80 kVp does appearing to be slightly more effective than 100 kVp (p=0.011, *). This data acquired from X-PACT treatment of 4T1-HER2 cells with constant phosphor concentration of 50 μg/mL and UVADEX diluted to 8-MOP concentration of 10 μM (1:10 dilution). N is the number of independent measurements. These experiments involved 4T1-HER2 cells treated with 10 μM 8-MOP (or equivalent UVADEX), and 50 μg/mL phosphors.

2.2 In-Vivo X-Pact Experiments

Figure 6:
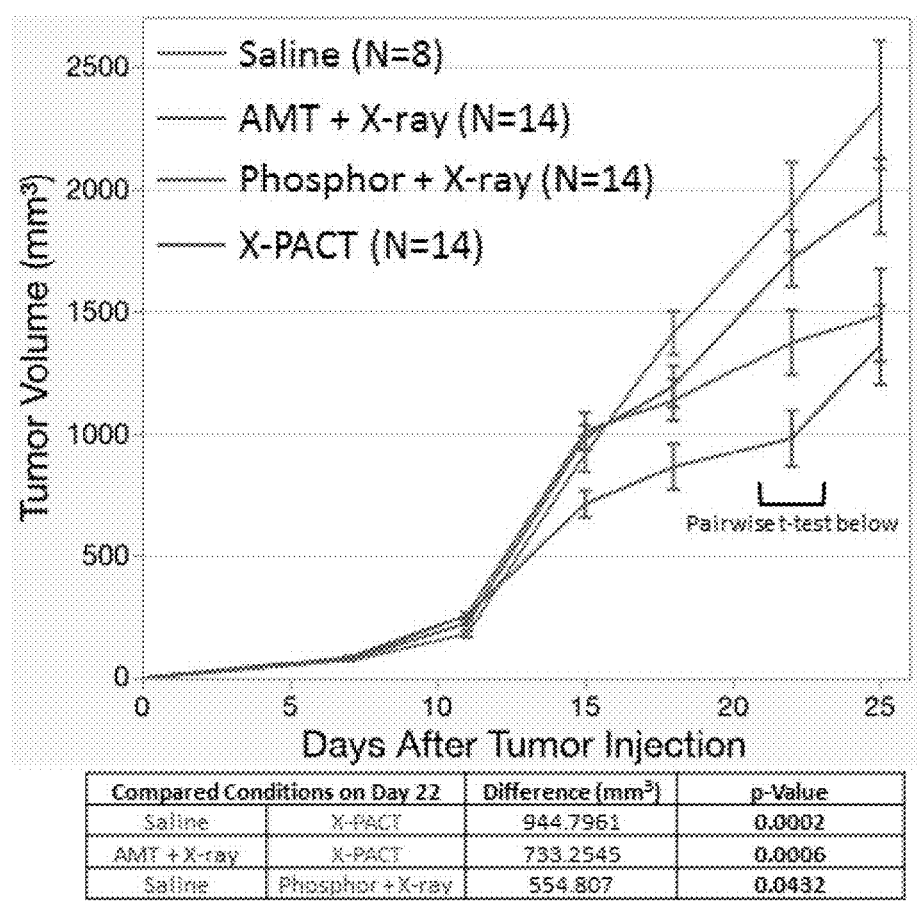
FIG. 6 is a schematic depicting the results of an X-PACT application to BALBC mice with syngeneic 4T1-HER2 tumors.

The results from the in-vivo irradiation of syngeneic 4T1-HER2 tumors are shown in FIG. 6. In this evaluation. X-PACT treatment was applied to BALBC mice with syngeneic 4T1-HER2 tumors. In the separate psoralen and phosphor control arms (blue and red respectively), 5 μM psoralen (AMT) and 100 μg of phosphor where applied. A consistent x-ray irradiation technique was used for all arms (except saline control) which was 2 Gy delivered at 75 kVp by 30 mA in 3 minutes.

3. Discussion

In the 4T1 in-vitro cell viability analysis (FIG. 2A), a very substantial reduction in viable cells (~48%, p<0.0001) was observed in the full X-PACT treatment condition, where all components (phosphor, psoralen, and x-ray) were present. Cell viability was much higher (70-85%) in the control conditions (left and middle bars in FIG. 2A). Interestingly, the effect of adding radiation to the control conditions shows no or only a small decrease in viability. Cells exposed to UVADEX alone (left bars in FIG. 2A) show no significant effect of adding radiation (p=0.97). Cells exposed to phosphors alone (middle bars in FIG. 2A) show a slight reduction in cell viability (~8%, p=0.034) when radiation is added. The increased toxicity associated with the presence of both phosphors and x-rays could be attributed to DNA damage arising by UV light from x-ray induced phosphorescence from the phosphors. Substantial cytotoxicity (~80%) was only observed in the full X-PACT arm demonstrating the synergistic therapeutic effect of the combination of phosphor, UVADEX and radiation.

In the 4T1 in-vitro apoptotic analysis (FIG. 2B), cells exposed to UVADEX alone (left bars exhibit negligible apoptotic activity either with or without x-ray. For cells exposed to phosphor alone (middle bars), a small increase in Annexin V signal is observed (~1%, p=0.098) again suggesting a slight toxicity of the phosphors. However, it was only when both phosphor and UVADEX are combined (right bars) that a statistically significant increase in Annexin V signal was observed (~8%, p<0.0001), indicating an increase in apoptosis. The cytotoxicity typical of X-PACT is further illustrated in the methyl blue staining in FIGS. 2C and 2D. In both the X-PACT 2 and X-PACT 3 conditions, a relatively small effect was observed for the individual components of UVADEX and phosphor. The methyl blue staining results were consistent with the flow cytometry data, in that all X-PACT components are required for high cytotoxicity. Less cytotoxicity is manifest in the first X-PACT condition because of decreased phosphor concentration.

When X-PACT and components were evaluated on 3 different cell lines (FIG. 3A), an ANOVA analyses reveals no statistically significant differences in the sensitivity of these lines either to individual components or to full X-PACT treatment (p>0.05). In CT2A malignant glioma cells, X-PACT cell cytotoxicity was observed (FIG. 3B) to increase with the magnitude of X-ray dose (0, 0.66 and 1 Gy respectively), concentration of 8-MOP psoralen (10, 20 and 40 μM respectively), and phosphor (50 and 100 μg/ml respectively). ANOVA analyses revealed that the effect of radiation on each condition was significant for all conditions except for the control (p=0.88). The effect of radiation dose was significant overall (p<0.001) and progressive (cell cytotoxicity increases with dose) for all conditions where >20 μM of 8-MOP and 50 μg/mL of phosphors were used. In one condition (10 μM 8-MOP+100 μg/ml phosphor) only weakly significant influence of radiation dose (0.01<p<0.05) was observed.

The most comprehensive in-vitro 4T1 analysis (FIG. 4) revealed a statistically significant multi-variable linear regression ($R^2$=0.72). The synergy interaction coefficient D was statistically significant (p<0.001) and positive indicating an enhanced effect when phosphor and psoralen were present. The interaction coefficients for psoralen and phosphor alone were only weakly suggestive (p~0.1 and 0.05 respectively). The p values indicate likely significance, but gave no indication of magnitude of effect, which is shown in FIG. 4B. A general observation from this data, acquired with constant x-ray dose, is that the apoptotic fraction induced by X-PACT increases with either increasing phosphor or psoralen concentration.

Another in-vitro study investigated whether changing x-ray energy affected X-PACT efficacy (FIG. 5). Phosphor design considerations indicated that ~80 kV would be optimal, but a higher energy would have an advantage from treatment delivery perspective (greater penetration in tissue). For this reason, a 100 kVp beam energy was investigated. An increase in apoptotic signal (over the control) was observed for X-PACT treatments at both energies. The data suggests the possibility of a slightly greater effect at 80 kVp.

X-PACT therapy seeks to engage the anti-tumor properties of psoralens activated in-situ, in solid tumors, with the potential for engaging a long term response. The data presented in FIG. 6, show the first in-vivo application. The first X-PACT treatment was delivered to the syngeneic 4T1-HER2 tumors, on day 10 after implantation. Over the next two weeks a growth delay was observed in the X-PACT treatment arm. By day 25, there was a 42% reduction in tumor volume (p=0.0002). A slightly higher component effect was observed for both the psoralen and phosphor arms, than was expected from the on-vitro data in FIG. 2.

Accordingly, in one embodiment of the invention, depending on the type of tumor being treated, the day-25 tumor volume change can range from stable (no growth), to a reduction of at least 10%, at least 20%, at least 30%, at least 40%, to complete dissolution of the tumor, or any values in between.

System Implementation

Figure 7:
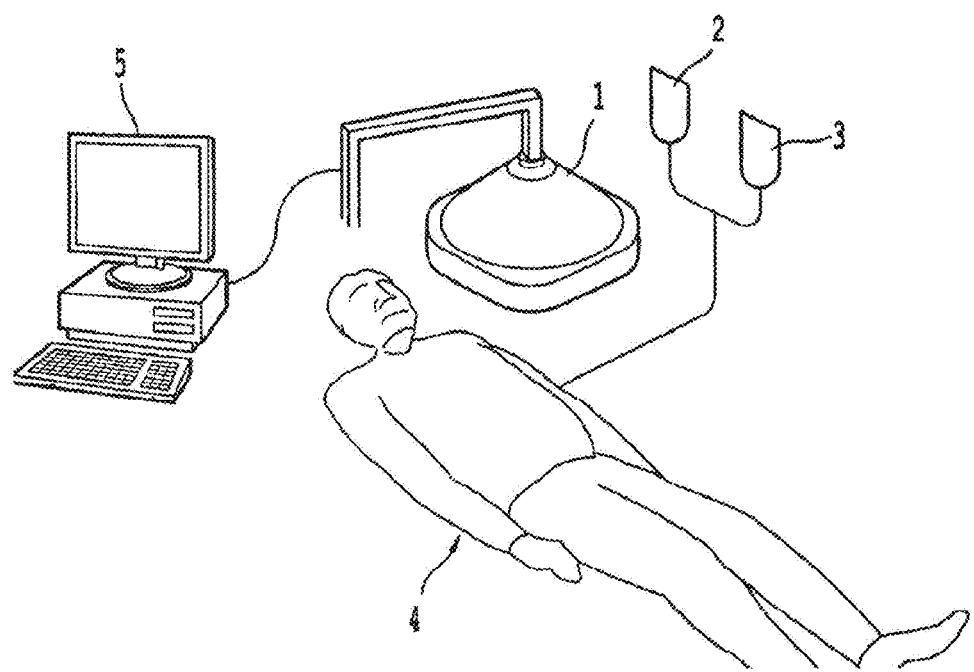
FIG. 7 is a schematic depicting an exemplary system according to one embodiment of the present invention.

The above-discussed medical treatments can be implemented by the system shown in FIG. 7.

Referring to FIG. 7, an exemplary system according to one embodiment of the present invention may have an initiation energy source 1 directed at the subject 4. An activatable pharmaceutical agent 2 and an energy modulation agent 3 are administered to the subject 4. The initiation energy source may additionally be controlled by a computer system 5 that is capable of directing the delivery of the initiation energy.

In preferred embodiments, the initiation energy source may be a linear accelerator equipped with image guided computer-control capability to deliver a precisely calibrated beam of radiation to a pre-selected coordinate. One example of such linear accelerators is the SmartBeam™ IMRT (intensity modulated radiation therapy) system from Varian medical systems (Varian Medical Systems, Inc., Palo Alto, Calif.). In one embodiment of the invention, the initiation energy source comprises an x-ray source configured to generate x-rays from a peak applied cathode voltage at or below 300 kVp, at or below 200 kVp, at or below 120 kVp, at or below 105 kVp, at or below 80 kVp, at or below 70 kVp, at or below 60 kVp, at or below 50 kVp, at or below 40 kVp, at or below 30 kVp, at or below 20 kVp, at or below 10 kVp, or at or below 5 kVp.

In one embodiment of the invention, besides the YTaO4, noted above, other energy modulation agents can include phosphors were obtained from the following sources. "Ruby Red" obtained from Voltarc, Masonlite & Kulka, Orange, Conn., and referred to as "Neo Ruby"; "Flamingo Red" obtained from EGL Lighting, Berkeley Heights, N.J. and referred to as "Flamingo"; "Green" obtained from EGL Lighting, Berkeley Heights, N.J. and referred to as "Tropic Green"; "Orange" obtained from Voltarc, Masonlite & Kulka, Orange, Conn., and referred to as "Majestic Orange"; "Yellow" obtained from Voltarc, Masonlite & Kulka, Orange, Conn., and referred to as "Clear Bright Yellow." The "BP" phosphors are shown in detail below:

TABLE 3

| Code | Phosphor Material Color | Emission Spectrum Peak Emission (nm) | X-Ray Absorption Emiss Eff (%) | Eff (Z) | K-edge (keV) | Density g/cc Specific Gravity | Xtal Crystal Structure | Hygroscopic |
|---|---|---|---|---|---|---|---|---|
| BP1 | CaWO4: Pb | 425 | | | | | | N |
| BP2 | Y2SiO5: Ce | 410 | | | | | | N |
| BP3 | YTaO4 | 337 | 10 | 59.8 | 67.42 | 7.5 | Monolithic | N |
| BP3-C | YTaO4 | 337 | 10 | 59.8 | 67.42 | 7.5 | Monolithic | N |
| BP4 | BASF-1 | 460 | | | | | | |
| BP5 | BASF-2 | 490 | | | | | | |
| BP6 | YTaO4: Nb (*) | 410 | 11 | 59.8 | 67.42 | 7.5 | Monolithic | N |
| BP6-C | YTaO4: Nb (*) | | | | | | | |
| BP7-C | LaOBr: Tm3+ (coated) | 360, 460 | 14 | 49.3 | 38.92 | 6.3 | Tetragonal | N |
| BP8-C | LaF3: Ce | 280 | | | | | | |
| BP9 | Y2O3 | 365 | | | | | | |
| BP-10 | BaSO4—: Eu2+ (coated) | 390 | 6 | 45.5 | 37.38 | 4.5 | Rhombic | N |
| BP10-C | BaSO4—: Eu2+ (coated) | 390 | 6 | 45.5 | 37.38 | 4.5 | Rhombic | N |
| BP11 | LaOCl: Tm | | | | | | | |
| BP12 | Y2O2S: Tm | | | | | | | |
| BP13 | BaSi2O5: Pb2+ | 350 | | | | | | N |
| | SrB6O10: Pb | 360 | | | | | | N |
| | CsI: Na (Coated) | 338 | | | | | | Y |
| | Gd2O2S: Tm | Blue to Green | | | | | | Y |

The "BP" phosphors are available from PhosphorTech Corporation of Kennesaw, Ga., from BASF Corporation, or from Phosphor Technology Ltd, Norton Park, Norton Road Stevenage, Herts, SGI 2BB, England.

Other useful energy modulation agents include semiconductor materials including for example $TiO_2$, ZnO, and $Fe_2O_3$ which are biocompatible, and CdTe and CdSe which would preferably be encapsulated because of their expected toxicity. Other useful energy modulation agents include ZnS, CaS, BaS, SrS and $Y_2O_3$ which are less toxic. Other suitable energy modulation agents which would seem the most biocompatible are zinc sulfide, $ZnS:Mn^{2+}$, ferric oxide, titanium oxide, zinc oxide, zinc oxide containing small amounts of $Al_2O_3$ and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles, $Yb^{3+}$ doped $CsMnCl_3$ and $RbMnCl_3$, $BaFBr:Eu^{2+}$ nanoparticles, cesium iodide, bismuth germanate, cadmium tungstate, and CsBr doped with divalent Eu. Table 4 below provides a list of various useful energy modulation agents In various embodiments of the invention, the following luminescent polymers are also suitable as energy modulation agents: poly(plienylene ethynylene), poly(phenylene vinylene), poly(p-phenylene), poly(thiophene), poly(pyridyl vinylene), poly(pyrrole), poly(acetylene), poly(vinyl carbazole), poly(fluorenes), and the like, as well as copolymers and/or derivatives thereof.

As a non-limiting list, the following are suitable energy modulation agents: $Y_2O_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn,Yb $ZnS:Tb^{3+}$, $Er^{3+}$; $ZnS:Tb^{3+}$; $Y_2O_3:Tb^{3+}$; $Y_2O_3:Tb^{3+}$, Er3+; $ZnS:Mn^{2+}$; ZnS:Mn, $Er^{3+}$; $CaWO_4$, $YaTO_4$, $YaTO_4:Nb$, $BaSO_4:Eu$, $La_2O_2S:Tb$, $BaSi_2O_5:Pb$, NaI(Tl), CsI(Tl), CsI(Na), CsI(pure), CsF, KI(Tl), LiI(Eu), $BaF_2$, CaF, $CaF_2(Eu)$, ZnS(Ag), $CaWO_4$, $CdWO_4$, YAG(Ce) ($Y_3Al_5O_{12}(Ce)$). BGO bismuth germanate, GSO gadolinium oxyorthosilicate, LSO lutetium oxyorthosilicate, $LaCl_3(Ce)$, $LaBr_3(Ce)$, $LaPO_4$; Ce, Tb (doped), $Zn_2SiO_4:Mn$ with Mn doped between 0.05-10%, and $YTaO_4$.

TABLE 4

| Phosphor | Emission Spectrum Peak Emmission (nm) | Emiss Eff (%) | Eff (Z) | X-Ray Absorption K-edge (keV) | Specific Gravity | Crystal Structure | Hygroscopic |
|---|---|---|---|---|---|---|---|
| Zn3(PO4)2: Tl+ | 310 | | | | | | N |
| BaF2 | 310 | | | | | | Slightly |
| CsI | 315 | | | | | | N |
| Ca3(PO4)2: Tl+ | 330 | | | | | | N |
| YTaO4 | 337 | | 59.8 | 67.42 | 7.5 | Monolithic | N |
| CsI: Na | 338 | | | | | | Y |
| BaSi2O5: Pb2+ | 350 | | | | | | N |
| Borosilicate | 350 | | | | | | N |
| LaCl3(Ce) | 350 | | | | | | Y |
| SrB4O7F: Eu2+ | 360 | | | | | | N |
| RbBr: Tl+ | 360 | | | | | | ? |
| (Ba, Sr, Mg)3Si2O7: Pb2+ | 370 | | | | | | N |
| YAlO3: Ce3+ | 370 | | | | | | N |
| BC-422 | 370 | | | | | Organic | ? |
| BaFCl: Eu2+ | 380 | 13 | 49.3 | 37.38 | 4.7 | Tetragonal | N |
| BaSO4—: Eu2+ | 390 | 6 | 45.5 | 37.38 | 4.5 | Rhombic | N |
| BaFBr: Eu2+ | 390 | | | | | | ? |
| BC-420 | 391 | | | | | Organic | ? |
| BC-414 | 392 | | | | | Organic | ? |
| SrMgP2O7: Eu2+ | 394 | | | | | | N |
| BaBr2: Eu2+ | 400 | | | | | | N |
| (Sr, Ba)Al2Si2O8: Eu2+ | 400 | | | | | | N |
| YTaO4: Nb (*) | 410 | 11 | 59.8 | 67.42 | 7.5 | Monolithic | N |
| Y2SiO5: Ce3+ | 410 | | | | | | N |
| CaWO4 | 420 | 5 | 61.8 | 69.48 | 6.1 | Tetragonal | N |
| LaOBr: Tb3+ | 420 | 20 | 49.3 | 38.92 | 6.3 | Tetragonal | N |
| Y2O2S: Tb3+ | 420 | 18 | 34.9 | 17.04 | 4.9 | Hexgonal | N |
| Lu2SiO5: Ce3+ | 420 | | | | | | N |
| Lu1.8 Y0.2SiO5: Ce | 420 | | | | | | N |
| ZnS: Ag | 450 | 17 | 26.7 | 9.66 | 3.9 | Hexgonal | N |
| CdWO4 | 475 | | | | | | Slightly |
| Bi4Ge3O12 (BGO) | 480 | | | | | | N |
| (Zn, Cd)S: Ag | 530 | 19 | 38.4 | 9.66/26.7 | 4.8 | Hexgonal | N |
| Gd2O2S: Tb3+ | 545 | 13 | 59.5 | 50.22 | 7.3 | Hexgonal | N |
| La2O2S: Tb3+ | 545 | 12.5 | 52.6 | 38.92 | 6.5 | Hexgonal | N |
| Y3Al5O12 (Ce) | 550 | | | | | | N |
| LaOBr: Tm3+ | 360, 460 | 14 | 49.3 | 38.92 | 6.3 | Tetragonal | N |
| CaF2(Eu) | 435/300 | | | | | | N |

In one embodiment, phosphors used in the invention as energy modulation agents can include phosphor particles, ionic doped phosphor particles, single crystal or poly-crystalline powders, single crystal or poly-crystalline monoliths, scintillator particles, a metallic shell encapsulating at least a fraction of a surface of the phosphors, a semiconductor shell encapsulating at least a fraction of a surface of the phosphors, and an insulator shell encapsulating at least a fraction of a surface of the phosphors; and phosphors of a distributed particle size.

In further embodiments, dose calculation and robotic manipulation devices may also be included in the system.

Figure 8:
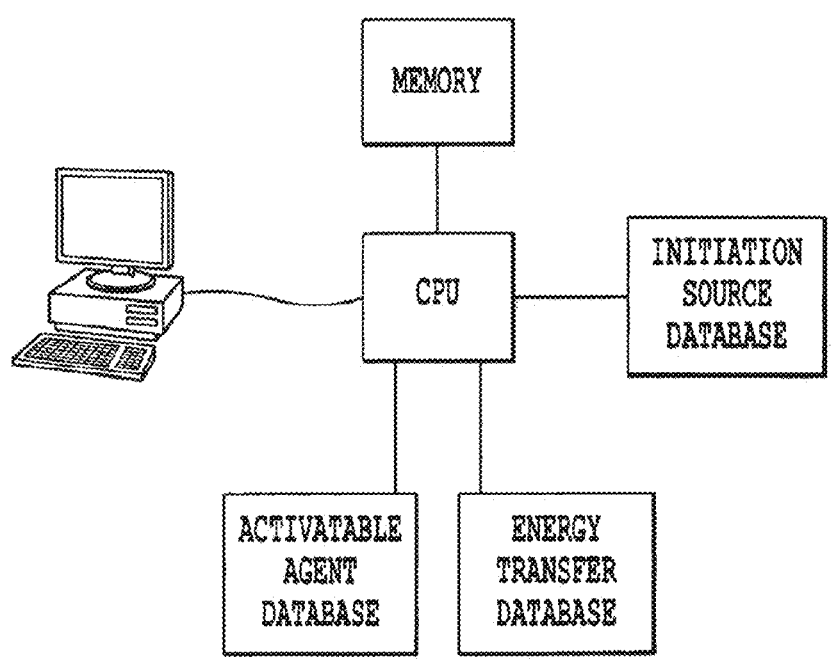
FIG. 8 is an exemplary computer-implemented system according to one embodiment of the present invention.

In yet another embodiment, there is also provided a computer implemented system for designing and selecting suitable combinations of initiation energy source (listed in the initiation energy source database), energy modulation agent (listed in the energy transfer database), and activatable pharmaceutical agent (listed in the activatable agent database). FIG. 8 illustrates an exemplary computer implemented system according to this embodiment of the present invention.

Referring to FIG. 8, an exemplary computer-implemented system according to one embodiment of the present invention may have a central processing unit (CPU) connected to a memory unit, configured such that the CPU is capable of processing user inputs and selecting a combination of initiation source, activatable pharmaceutical agent, and energy transfer agent based on an energy spectrum comparison for use in a method of the present invention.

In one embodiment, a photoactivatable drug is selected from psoralens, pyrene cholesteryloleate, acridine, porphyrin, fluorescein, rhodamine, 16-diazorcortisone, ethidium, transition metal complexes of blcomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones.

In one embodiment of the invention, one or more "booster" treatments, follow the initial treatment considered a "priming treatment. A "booster treatment" in one embodiment could involve re-injecting the tumor with psoralen (or other photoactivatable drug) and radiating the tumor site again. A "booster treatment" in another embodiment could involve re-injecting the tumor with psoralen (or other photoactivatable drug) and an energy modulation agent and radiating the tumor site again. A "booster treatment" in another embodiment could involve radiating the tumor site again, but at a radiation level considered to be at either a palliative or therapeutic level. The purpose of any of these "booster" treatments is to activate the immune response initially or originally generated within the patient during the initial treatments.

In one embodiment of the booster treatment, the phosphor concentration is increased to 20 mg/mL, the amount of UVADEX is increased 2-4 times, and the treatment frequency is increased to five (5) treatments in five (5) consecutive days. Furthermore, the timing between the prime (initial treatment sessions such as the nine treatments described above) and the booster treatment is set to allow for an initial humoral or cellular immune response, followed by a period of homeostasis, most typically weeks or months after the initial priming treatment.

In another embodiment, particularly for more aggressive cancers, an intervening treatment between the prime and boost stages can be provided to stunt the growth of the tumor while the immune system develops a response. The intervening treatment can take the form of palliative radiation, or other treatments known to those skilled in the art. A "booster treatment" in a further embodiment can involve irradiating a different tumor site within the patient (such as a metastasis site), at a radiation level considered to be at either a palliative or therapeutic level or at a radiation induced cell kill level. Since the goal of the "booster treatments" is to activate the patient's immune system, any of the "booster treatments" can be pertained after completion of all of the primer treatments, between primer treatments during a series of the primer treatments, or prior to the primer treatments (although this may seem odd to perform the primer treatment after the booster treatment, the booster treatment can activate the immune system, thus providing a boost to the primer treatment once performed).

While not limited to the following theory, the basic prime-boost strategy involves priming the immune system to a target antigen, or a plurality of antigens created by the drug and/or radiation induced cell kill and then selectively boosting this immunity by re-exposing the antigen or plurality of antigens in the boost treatment. One aspect of this strategy is that greater levels of immunity are established by heterologous prime-boost than can be attained by a single vaccine administration or homologous boost strategies. For example, the initial priming events elicited by a first exposure to an antigen or a plurality of antigens appear to be imprinted on the immune system. This phenomenon is particularly strong in T cells and is exploited in prime-boost strategies to selectively increase the numbers of memory T cells specific for a shared antigen in the prime and boost vaccines. As described in the literature, these increased numbers of T cells 'push' the cellular immune response over certain thresholds that are required to fight specific pathogens or cells containing tumor specific antigens. Furthermore, the general avidity of the boosted T-cell response is enhanced, which presumably increases the efficacy of the treatment.

Here, in this invention and without limitation as to the details but rather for the purpose of explanation, the initial treatment protocol develops antibodies or cellular immune responses to the psoralen-modified or X-ray modified cancer cells. These "initial" responses can then be stimulated by the occurrence of a large number of newly created psoralen-modified or X-ray modified cancer cells. As such, the patient's immune system would mount a more robust response against the cancer than would be realized in a single treatment series.

In one embodiment of the invention, cancer cells can be removed from a diseased site in the patient, and then treated ex-vivo with psoralen and ultraviolet light to induce cell kill. The "killed" cancer cells are then as part of an initial treatment or a booster treatment injected into the disease region of the patient. In one embodiment of the invention, the removed cancer cells are cultured to provide a larger number of cells to be exposed to psoralen and ultraviolet light, and therefore to produce a larger number of "killed" cells to inject. The body in response to these "killed" cells (in a manner similar to how the psoralen-modified or X-ray modified cancer cells would be received) would trigger the patient's immune system.

In one embodiment of the invention, prior to the initial treatment or prior to booster treatments, the immune system of the subject could be further stimulated by injection of a more conventional vaccine such as for example a tetanus vaccine. Prior work has shown the efficacy of a tetanus booster to bolster the immune system's attack on the tumor by helping cancer vaccines present in the subject migrate to the lymph nodes, activating an immune response. Here, in this invention, the autovaccines generated internally from the treatments described above could also benefit from this effect.

In a further embodiment, methods in accordance with the present invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

The activatable pharmaceutical agent and derivatives thereof as well as the energy modulation agent, can be incorporated into pharmaceutical compositions suitable for administration. Such compositions typically comprise the activatable pharmaceutical agent and a pharmaceutically acceptable carrier. The pharmaceutical composition also comprises at least one additive having a complementary therapeutic or diagnostic effect, wherein the additive is one selected from an antioxidant, an adjuvant, or a combination thereof.

As used herein, pharmaceutically acceptable carrier is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the compound of the present invention to affect solubility or clearance of the compound. These molecules may also be synthesized with D-amino acids to increase resistance to enzymatic degradation. If necessary, the activatable pharmaceutical agent can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. The oral compositions can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery. In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

It will also be understood that the order of administering the different agents is not particularly limited. Thus in some embodiments the activatable pharmaceutical agent may be administered before the energy modulation agent, while in other embodiments the energy modulation agent may be administered prior to the activatable pharmaceutical agent. It will be appreciated that different combinations of ordering may be advantageously employed depending on factors such as the absorption rate of the agents, the localization and molecular trafficking properties of the agents, and other pharmacokinetics or pharmacodynamics considerations.

In one embodiment of the invention, the reagents and chemicals useful for methods and systems of the present invention may be packaged in kits to facilitate application of the present invention. In one exemplary embodiment, a kit including a psoralen, and fractionating containers for easy fractionation and isolation of autovaccines is contemplated. A further embodiment of kit would comprise at least one activatable pharmaceutical agent capable of causing a predetermined cellular change, at least one energy modulation agent capable of activating the at least one activatable agent when energized, and containers suitable for storing the agents in stable form, and preferably further comprising instructions for administering the at least one activatable pharmaceutical agent and at least one energy modulation agent to a subject, and for applying an initiation energy from an initiation energy source to activate the activatable pharmaceutical agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

Statements of the Invention:

The following enumerated statements describe generalized aspects of the invention and are not provided to limit the invention beyond that which is expressly provided in the appended claims.

Statement 1. A system (and method) for treating a diseased sited in a human or animal body, comprising:
a pharmaceutical carrier including one or more phosphors or energy converters which are capable of emitting ultraviolet or visible light into the body;
a photoactivatable drug for intercalating into DNA of cells at the diseased site; one or more devices which infuse a diseased site with the photoactivatable drug and the pharmaceutical carrier;
an initiation energy source comprising an x-ray or high energy source (electron beam) which irradiates the diseased site with at least one of x-rays, gamma rays, or electrons to thereby initiate emission of said ultraviolet or visible light into the body; and
a processor programmed to control a dose of said x-rays, gamma rays, or electrons to the diseased site for production of said ultraviolet or visible light at the diseased site to activate the photoactivatable drug, wherein the infusion of the photoactivatable drug and the phosphors into the diseased site and the dose of x-rays or electron beam produces a cytotoxicity inside the diseased site of greater than 20%, greater than 20%, greater than 30%, greater than 50%, greater than 60%, greater than 70%, or greater than 80%.

The associated method of statement 1 injects into a vicinity of and inside the tumor (or a diseased site) a pharmaceutical carrier including one or more phosphors which are capable of emitting light into the tumor or the body upon interaction, infuses the tumor with a photoactivatable drug for intercalating into DNA of cells at the diseased site, applying x-ray or high energy electrons to the tumor (or a diseased site), and produces the light inside the tumor (or a diseased site) to activate the photoactivatable drug and produce, wherein the injection of the photoactivatable drug and the phosphors and the dose of x-rays or electrons produces a cytotoxicity inside the diseased site of greater than 20%, Statement 2. The system (or associated method) of statement 1, wherein the initiation energy source comprises an x-ray source configured to generate x-rays from a peak applied cathode voltage at or below 300 kVp, at or below 200 kVp, at or below 120 kVp, at or below 105 kVp, at or below 80 kVp, at or below 70 kVp, at or below 60 kVp, at or below 50 kVp, at or below 40 kVp, at or below 30 kVp, at or below 20 kVp, at or below 10 kVp, or at or below 5 kVp.

Statement 3. The system (or associated method) of statement 1, wherein the phosphors are injected nearby the diseased site for illumination of the photoactivatable drug to treat the diseased site.

Statement 4. The system (or associated method) of statement 3, wherein the phosphors injected nearby the diseased site comprise a mixture of micron-size and nanometer-size particles.

Statement 5. The system (or associated method) of statement 1, wherein the phosphors comprise at least one of: phosphor particles; ionic doped phosphor particles; single crystal or poly-crystalline powders; single crystal or poly-crystalline monoliths; scintillator particles; a metallic shell encapsulating at least a fraction of a surface of the phosphors; a semiconductor shell encapsulating at least a fraction of a surface of the phosphors; and an insulator shell encapsulating at least a fraction of a surface of the phosphors; and phosphors of a distributed particle size.

Statement 6. The system (or associated method) of statement 1, wherein the phosphors comprise at least one of $Y_2O_3$; ZnS; ZnSe; MgS; CaS:Mn, Er ZnSe; Mn, Er MgS;

Mn, Er CaS; Mn, Er ZnS; Mn,Yb ZnSe; Mn,Yb MgS; Mn, Yb CaS; Mn,Yb ZnS:Tb$^{3+}$, Er$^{3+}$; ZnS:Tb$^{3+}$; Y$_2$O$_3$:Tb$^{3+}$; Y$_2$O$_3$:Tb$^{3+}$, Er$^{3+}$; ZnS:Mn$^{2+}$; ZnS:Mn, Er$^{3+}$; CaWO$_4$, YaTO$_4$, YaTO$_4$:Nb, BaSO$_4$:Eu, La$_2$O$_2$S:Tb, BaSi$_2$O$_5$:Pb, NaI(Tl), CsI(Tl), CsI(Na), CsI(pure), CsF, KI(Tl), LiI(Eu), BaF$_2$, CaF, CaF$_2$(Eu), ZnS(Ag), CaWO$_4$, CdWO$_4$, YAG(Ce) (Y$_3$Al$_5$O$_{12}$(Ce)), BGO bismuth gemianate, GSO gadolinium oxyorthosilicate, LSO lutetium oxyorthosilicate, LaCl$_3$(Ce), LaBr$_3$(Ce), LaPO$_4$; Ce, Tb (doped), Zn$_2$SiO$_4$:Mn with Mn doped between 0.05-10%, and YTaO$_4$.

Statement 7. The system (or associated method) of statement 1, wherein the phosphors comprise down conversion media, and agglomerations thereof with or without plasmonic agents.

Statement 8. The system (or associated method) of statement 1, wherein the one or more devices administer the photoactivatable drug in accordance with a volume of the diseased site.

Statement 9. The system (or associated method) of statement 8, wherein an amount of the phosphors in the pharmaceutical carrier ranges from 0.1 to 0.66 milligrams of phosphor per cm$^3$ of the volume of the diseased site, and a concentration of the photoactivatable drug in the pharmaceutical carrier ranges from 10 µg/mL to 50 µg/mL.

Statement 10. The system (or associated method) of statement 1, wherein the photoactivatable drug comprises a psoralen compound mixed with the phosphors.

Statement 11. The system (or associated method) of statement 1, wherein the photoactivatable drug is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones.

Statement 12. The system (or associated method) of statement 1, wherein the photoactivatable drug comprises a psoralen, a coumarin, a porphyrin or a derivative thereof.

Statement 13. The system (or associated method) of statement 1, wherein the photoactivatable drug comprises s 8-MOP, TMP, or AMT.

Statement 14. The system (or associated method) of statement 1, wherein the photoactivatable drug comprises one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematophorphyrin, and phthadocyanine.

Statement 15. The system (or associated method) of statement 1, wherein the photoactivatable drug is coupled to a earlier that is capable of binding to a receptor at the diseased site.

Statement 16. The system (or associated method) of statement 15, wherein the carrier is one selected from insulin, interleukin, thymopoietin or transferrin.

Statement 17. The system (or associated method) of statement 15, wherein the receptor is one selected from nucleic acids of nucleated cells, antigenic sites on nucleated cells, or epitopes.

Statement 18. The system (or associated method) of statement 1, wherein the photoactivatable drug has an affinity for a tumor at the diseased site.

Statement 19. The system (or associated method) of statement 18, wherein the photoactivatable drug is capable of being absorbed by a tumor at the diseased site.

Statement 20. The system (or associated method) of statement 19, wherein the photoactivatable drug is a DNA intercalator or a halogenated derivative thereof.

Statement 21. The system (or associated method) of statement 1, wherein the initiation energy source delivers a controlled radiation dose to the phosphors for activation of the photoactivatable drug.

Statement 22. The system (or associated method) of statement 21, wherein the controlled radiation dose causes an auto-vaccine effect in the human or animal body.

Statement 23. The system (or associated method) of statement 1, wherein the processor controls the x-ray or high energy source during a booster treatment repeated on a periodic basis after an initial treatment of the diseased site.

Statement 24. The system (or associated method) of statement 23, wherein, in the booster treatment, at least one of phosphor concentration, photoactivatable drug concentration, and the radiation dose is increased by a factor of at least two times, five times, or ten times respective initial values.

Statement 25. The system (or associated method) of statement 23, wherein the booster treatment produces psoralen-modified cancer cells or X-ray modified cancer cells.

Statement 26. The system (or associated method) of statement 23, wherein the booster treatment produces radiation damaged cancer cells.

Statement 27. The system (or associated method) of statement 23, wherein a period between booster treatments is delayed according to a tolerance level of the human or animal body for radiation-modified cells generated during the booster treatment.

Statement 28. The system (or associated method) of statement 27, wherein the period between booster treatments is delayed such that no tolerance is developed for the radiation-modified cells.

Statement 29. The system (or associated method) of statement 1, wherein the initiation energy source directs radiation to at least one of a tumor or a malignancy.

Statement 30. The system (or associated method) of statement 1, wherein the initiation energy source directs radiation to at least one of a eukaryotic cell, a prokaryotic cell, a subcellular structure, an extracellular structure, a virus or prion, a cellular tissue, a cell membrane, a nuclear membrane, cell nucleus, nucleic acid, mitochondria, ribosome, or other cellular organelle.

Statement 31. The system (or associated method) of statement 1, wherein the initiation energy source directs said radiation to the diseased site in a pulsed manner having an on and off time.

Statement 32. The system (or associated method) of statement 1, wherein the initiation energy source directs said radiation to a tumor or a malignancy in a pulsed manner having an on and off time.

Statement 33. The system (or associated method) of statement 32, wherein the initiation energy source directs said radiation to the diseased site such that the on time activates the phosphor and the off time is long enough for decay of phosphor light emission.

Statement 34. The system (or associated method) of statement 1, wherein the initiation energy source directs said radiation to the diseased site according to a predetermined radiation protocol such that a predetermined change occurs in the diseased site.

Statement 35. The system (or associated method) of statement 34, wherein said predetermined change at least one of 1) affects a prion, viral, bacterial, fungal, or parasitic infection, 2) comprises at least one of one of tissue regeneration, inflammation relief, pain relief, immune system fortification, or 3) comprises at least changes in cell membrane permeability, up-regulation and down-regulation of adenosine triphosphate and nitric oxide.

Statement 36. A system for treating a diseased sited in a human or animal body, comprising:
 a pharmaceutical carrier including one or more phosphors which are capable of emitting ultraviolet or visible light into the body;
 a photoactivatable drug for intercalating into DNA of cells at the diseased site;
 one or more devices which infuse a diseased site with the photoactivatable drug and the pharmaceutical carrier;
 an initiation energy source comprising an x-ray or high energy source which irradiates the diseased site with at least one of x-rays, gamma rays, or electrons to thereby initiate emission of said ultraviolet or visible light into the body; and
 a processor programmed to control a dose of said x-rays, gamma rays, or electrons to the diseased site for production of said ultraviolet or visible light at the diseased site to activate the photoactivatable drug, wherein the infusion of the photoactivatable drug and the phosphors and the dose of x-rays or electron beam produce a day-25 stable tumor volume.

The associated method of statement 36 injects into a vicinity of and inside the tumor (or a diseased site) a pharmaceutical carrier including one or more phosphors which are capable of emitting light into the tumor or the body upon interaction, infuses the tumor with a photoactivatable drug for intercalating into DNA of cells at the diseased site, applying x-ray or high energy electrons to the tumor (or a diseased site), and produces the light inside the tumor (or a diseased site) to activate the photoactivatable drug and produce, wherein the injection of the photoactivatable drug and the phosphors into the diseased site and the dose of x-rays or electrons produces a cytotoxicity inside the diseased site of greater than 20%.

Statement 37. The system (or associated method) of statement 36, wherein the infusion of the photoactivatable drug and the phosphors and the dose of x-rays or electron beam produces a day-25 tumor volume reduction of at least 10%, or least 20%, or at least 30%, or least 40%, or least 50%.

Statement 38. The system (or associated method) of statement 36, wherein the infusion of the photoactivatable drug and the phosphors and the dose of x-rays or electrons produces a day-25 complete tumor remission.

Numerous modifications and variations of the invention are possible in light of the above teachings. It is therefore to be understood that within the scope of the appended claims, the invention may be practiced otherwise than as specifically described herein. All of the publications, references, patents, patent applications, and other documents identified above are incorporated by reference herein in their entirety.

The invention claimed is:

1. A system for treating a diseased site in a human or animal body, comprising:
 a pharmaceutical carrier including one or more phosphors which are capable of emitting ultraviolet or visible light into the body;
 a photoactivatable drug for intercalating into DNA of cells at the diseased site;
 one or more devices which are configured to infuse the diseased site with the photoactivatable drug and the pharmaceutical carrier;
 an initiation energy source comprising an x-ray source which is configured to irradiate the diseased site with x-rays to thereby initiate emission of said ultraviolet or visible light into the body; and
 a processor programmed to control a dose of said x-rays to the diseased site for production of said ultraviolet or visible light at the diseased site to activate the photoactivatable drug, wherein the infusion of the photoactivatable drug and the phosphors into the diseased site and the dose of x-rays produces a cytotoxicity inside the diseased site of greater than 20%,
 wherein an amount of the phosphors in the pharmaceutical carrier ranges from 0.1 to 0.66 milligrams of phosphor per $cm^3$ of the volume of the diseased site, and a concentration of the photoactivatable drug in the pharmaceutical carrier ranges from 10 µg/mL to 50 µg/mL; and
 wherein the processor is programmed to apply the x-rays to the diseased site in a pulsed manner, wherein the x-rays are delivered in either (i) a radiograph mode where multiple pulses of a set mA and ms are delivered every 5-15 seconds, or (ii) a pulsed fluoroscopy mode at a maximum mA setting.

2. The system of claim 1, wherein the initiation energy source comprises an x-ray source configured to generate x-rays from a peak applied cathode voltage at or below 300 kVp.

3. The system of claim 2, wherein the initiation energy source comprises an x-ray source configured to generate x-rays from a peak applied cathode voltage at or below 200 kVp.

4. The system of claim 2, wherein the initiation energy source comprises an x-ray source configured to generate x-rays from a peak applied cathode voltage at or below 120 kVp.

5. The system of claim 2, wherein the initiation energy source comprises an x-ray source configured to generate x-rays from a peak applied cathode voltage at or below 105 kVp.

6. The system of claim 2, wherein the initiation energy source comprises an x-ray source configured to generate x-rays from a peak applied cathode voltage at or below 80 kVp.

7. The system of claim 1, wherein the phosphors are configured to be injected nearby the diseased site for illumination of the photoactivatable drug to treat the diseased site.

8. The system of claim 7, wherein the phosphors comprise a mixture of micron-size and nanometer-size particles.

9. The system of claim 1, wherein the phosphors comprise at least one of:
 phosphor particles;
 ionic doped phosphor particles;
 single crystal or poly-crystalline powders;
 single crystal or poly-crystalline monoliths;
 scintillator particles;
 a metallic shell encapsulating at least a fraction of a surface of the phosphors;
 a semiconductor shell encapsulating at least a fraction of a surface of the phosphors;
 an insulator shell encapsulating at least a fraction of a surface of the phosphors; and
 phosphors of a distributed particle size.

10. The system of claim 1, wherein the phosphors comprise at least one of $Y_2O_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS: Mn, $Er^{3+}$; $CaWO_4$, $YaTO_4$, $YaTO_4$:Nb, $BaSO_4$:Eu, $La_2O_2S$: Tb, $BaSi_2O_5$:Pb, NaI(Tl), CsI(Tl), CsI(Na), CsI(pure), CsF, KI(Tl), LiI(Eu), $BaF_2$, CaF, $CaF_2$(Eu), ZnS(Ag), $CaWO_4$, $CdWO_4$, YAG(Ce) ($Y_3Al_5O_{12}$(Ce)), BGO bismuth germanate, GSO gadolinium oxyorthosilicate, LSO lutetium oxyorthosilicate, $LaCl_3$(Ce), $LaBr_3$(Ce), $LaPO_4$; Ce, Tb (doped), $Zn_2SiO_4$:Mn with Mn doped between 0.05-10%, and $YTaO_4$.

11. The system of claim 1, wherein the phosphors comprise down conversion media, and agglomerations thereof with or without plasmonic agents.

12. The system of claim 1, wherein the photoactivatable drug comprises a psoralen compound mixed with the phosphors.

13. The system of claim 1, wherein the photoactivatable drug is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones.

14. The system of claim 1, wherein the photoactivatable drug comprises a psoralen, a coumarin, a porphyrin or a derivative thereof.

15. The system of claim 1, wherein the photoactivatable drug comprises 8-MOP, TMP, or AMT.

16. The system of claim 1, wherein the photoactivatable drug comprises one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematoporphyrin, and phthadocyanine.

17. The system of claim 1, wherein the photoactivatable drug is coupled to a carrier that is capable of binding to a receptor at the diseased site.

18. The system of claim 17, wherein the carrier is one selected from insulin, interleukin, thymopoietin or transferrin.

19. The system of claim 17, wherein the receptor is one selected from nucleic acids of nucleated cells, antigenic sites on nucleated cells, or epitopes.

20. The system of claim 1, wherein the photoactivatable drug has an affinity for a tumor at the diseased site.

21. The system of claim 20, wherein the photoactivatable drug is capable of being absorbed by a tumor at the diseased site.

22. The system of claim 21, wherein the photoactivatable drug is a DNA intercalator or a halogenated derivative thereof.

23. The system of claim 1, wherein the initiation energy source is configured to deliver a controlled radiation dose to the phosphors for activation of the photoactivatable drug.

24. The system of claim 23, wherein the controlled radiation dose causes an auto-vaccine effect in the human or animal body.

25. The system of claim 1, wherein the processor is configured to control the x-ray or source during a booster treatment repeated on a periodic basis after an initial treatment of the diseased site.

26. The system of claim 1, wherein the initiation energy source is configured to direct radiation to at least one of a tumor or a malignancy.

27. The system of claim 1, wherein the initiation energy source is configured to direct radiation to at least one of a eukaryotic cell, a prokaryotic cell, a subcellular structure, an extracellular structure, a virus or prion, a cellular tissue, a cell membrane, a nuclear membrane, cell nucleus, nucleic acid, mitochondria, ribosome, or other cellular organelle.

28. The system of claim 1, wherein the initiation energy source is configured to direct said x-rays to the diseased site in a pulsed manner having an on and off time such that the on time activates the phosphors and the off time is long enough for decay of phosphor light emission.

29. The system of claim 1, wherein the initiation energy source is configured to direct said x-rays to the diseased site according to a predetermined radiation protocol such that a predetermined change occurs in the diseased site.

30. The system of claim 29, wherein
said predetermined change at least one of 1) affects a prion, viral, bacterial, fungal, or parasitic infection, 2) comprises at least one of one of tissue regeneration, inflammation relief, pain relief, immune system fortification, or 3) comprises at least changes in cell membrane permeability, up-regulation and down-regulation of adenosine triphosphate and nitric oxide.

31. A system for treating a diseased sited site in a human or animal body, comprising:
a pharmaceutical carrier including one or more phosphors which are capable of emitting ultraviolet or visible light into the body;
a photoactivatable drug for intercalating into DNA of cells at the diseased site;
one or more devices which are configured to infuse the diseased site with the photoactivatable drug and the pharmaceutical carrier;
an initiation energy source comprising an x-ray source which is configured to irradiate the diseased site with x-rays to thereby initiate emission of said ultraviolet or visible light into the body; and a processor programmed to control a dose of said to the diseased site for production of said ultraviolet or visible light at the diseased site to activate the photoactivatable drug, wherein the infusion of the photoactivatable drug and the phosphors into the diseased site and the dose of x-rays produces a day-25 stable tumor volume,
wherein an amount of the phosphors in the pharmaceutical carrier ranges from 0.1 to 0.66 milligrams of phosphor per $cm^3$ of the volume of the diseased site, and a concentration of the photoactivatable drug in the pharmaceutical carrier ranges from 10 µg/mL to 50 µg/mL; and
wherein the processor is programmed to apply the x-rays to the diseased site in a pulsed manner, wherein the x-rays are delivered in either (i) a radiograph mode where multiple pulses of a set mA and ms are delivered every 5-15 seconds, or (ii) a pulsed fluoroscopy mode at a maximum mA setting.

32. The system of claim 31, wherein the infusion of the photoactivatable drug and the phosphors and the dose of x-rays or electrons produces a day-25 tumor volume reduction of at least 10%.

33. The system of claim 31, wherein the infusion of the photoactivatable drug and the phosphors and the dose of x-rays or electrons produces a day-25 complete tumor remission.

34. The system of claim 31, wherein the infusion of the photoactivatable drug and the phosphors and the dose of x-rays or electrons produces a day-25 tumor volume reduction of at least 20%.

35. The system of claim 31, wherein the infusion of the photoactivatable drug and the phosphors and the dose of x-rays or electrons produces a day-25 tumor volume reduction of at least 30%.

36. The system of claim 31, wherein the infusion of the photoactivatable drug and the phosphors and the dose of x-rays or electrons produces a day-25 tumor volume reduction of at least 40%.

37. The system of claim 31, wherein the infusion of the photoactivatable drug and the phosphors and the dose of x-rays or electrons produces a day-25 tumor volume reduction of at least 50%.

* * * * *

UNITED STATES PATENT AND TRADEMARK OFFICE
CERTIFICATE OF CORRECTION

PATENT NO. : 11,305,131 B2
APPLICATION NO. : 16/554831
DATED : April 19, 2022
INVENTOR(S) : Oldham et al.

It is certified that error appears in the above-identified patent and that said Letters Patent is hereby corrected as shown below:

On the Title Page

Column 1, item (60) under "Related U.S. Application Data", delete "(60)" and insert -- (62) --, therefor.

In the Specification

In Column 10, Line 31, delete "ill-vitro" and insert -- in-vitro --, therefor.

In Column 14, Line 13, delete "YTaO4," and insert -- $YTaO_4$, --, therefor.

In Column 15, Line 66, delete "poly(plienylene" and insert -- poly(phenylene --, therefor.

In Column 17, Line 21, delete "blcomycin," and insert -- bleomycin, --, therefor.

In Column 17, Line 66, delete "pertained" and insert -- performed --, therefor.

In Column 20, Line 6, delete "manitol," and insert -- mannitol, --, therefor.

In Column 23, Lines 52-53, delete "tetrasulonate, hematophorphyrin, and phthadocyanine." and insert -- tetrasulfonate, hematoporphyrin, and phthalocyanine. --, therefor.

In Column 23, Line 56, delete "earlier" and insert -- carrier --, therefor.

In the Claims

In Column 27, Claim 16, Lines 42-43, delete "tetrasulonate," and insert -- tetrasulfonate, --, therefor.

Signed and Sealed this
Eleventh Day of October, 2022

*Katherine Kelly Vidal*

Katherine Kelly Vidal
*Director of the United States Patent and Trademark Office*

CERTIFICATE OF CORRECTION (continued)
U.S. Pat. No. 11,305,131 B2

In Column 27, Claim 16, Line 43, delete "phthadocyanine." and insert -- phthalocyanine. --, therefor.

In Column 28, Claim 25, Line 2, delete "or".